(12) United States Patent
Ben-Noon et al.

(10) Patent No.: US 12,708,742 B2
(45) **Date of Patent: *Aug. 18, 2026**

(54) TRANSFORMABLE DUAL LUMEN CANNULA INTO A SINGLE LUMEN CANNULA AND METHODS OF USE

(71) Applicant: Inspira-Technologies OXY B.H.N. LTD., Ra'anana (IL)

(72) Inventors: Dagi Ben-Noon, Burgata (IL); Abraham Shabtay, Tel-Aviv (IL); Adi Rizansky Nir, Herzlyia (IL)

(73) Assignee: Inspira-Technologies OXY B.H.N.LTD., Ra'anana (IL)

( * ) Notice: Subject to any disclaimer, the term of this patent is extended or adjusted under 35 U.S.C. 154(b) by 891 days.

This patent is subject to a terminal disclaimer.

(21) Appl. No.: 18/062,610

(22) Filed: Dec. 7, 2022

(65) Prior Publication Data

US 2023/0095678 A1 Mar. 30, 2023

Related U.S. Application Data

(63) Continuation-in-part of application No. 17/523,811, filed on Nov. 10, 2021, now Pat. No. 11,541,159.

(Continued)

(51) Int. Cl.

*A61M 25/00* (2006.01)
*A61M 1/16* (2006.01)

(Continued)

(52) U.S. Cl.

CPC ........ *A61M 25/003* (2013.01); *A61M 1/1698* (2013.01); *A61M 25/0028* (2013.01);

(Continued)

(58) Field of Classification Search

CPC .............. A61M 1/1698; A61M 1/3659; A61M 1/3661; A61M 25/0028; A61M 25/0029;

(Continued)

(56) References Cited

U.S. PATENT DOCUMENTS 5,053,004 A 10/1991 Markel et al.
5,718,678 A 2/1998 Fleming, III (Continued)

FOREIGN PATENT DOCUMENTS

WO 2005/035022 A2 4/2005

OTHER PUBLICATIONS

International Preliminary Report on Patentability (Chapter I) for PCT/IL2021/051335, May 16, 2023.

*Primary Examiner* — Wesley G Harris
*Assistant Examiner* — Charles W Nichols
(74) *Attorney, Agent, or Firm* — Guy Levi (Ph.D.)

(57) ABSTRACT

The present invention is directed to a dual lumen cannula configured to be inserted into a patient's body as simple as a single lumen cannula. The dual lumen cannula includes at least one inner lumen configured to be inserted into an outer lumen and connected via an inner lumen connection unit and an outer unit connection unit. Embodiments of the presenting invention further allow for the connection of at least one flow router to the other end of the inner lumen connection unit. When installed, the outer lumen is first inserted into the patient's body, followed by the insertion of the inner lumen into the outer lumen of the already cannulated patient until the inner lumen connector unit is in coupling contact with the outer lumen connector unit. The invention is also directed to a transformable dual lumen cannula into a single lumen cannula and vice versa that allow patients that are first being treated by low flow approach to be treated by high flow approach.

20 Claims, 16 Drawing Sheets

Related U.S. Application Data

(60) Provisional application No. 63/338,787, filed on May 5, 2022, provisional application No. 63/111,803, filed on Nov. 10, 2020, provisional application No. 63/111,813, filed on Nov. 10, 2020.

(51) Int. Cl.
*A61M 25/02* (2006.01)
*A61M 25/06* (2006.01)
*A61M 39/10* (2006.01)

(52) U.S. Cl.
CPC ........ *A61M 25/0029* (2013.01); *A61M 25/02* (2013.01); *A61M 25/0637* (2013.01); *A61M 39/105* (2013.01); *A61M 2025/0286* (2013.01); *A61M 2205/70* (2013.01)

(58) Field of Classification Search
CPC ............ A61M 25/003; A61M 25/0039; A61M 39/105; A61M 2025/0286; A61M 2025/0031; A61M 2025/0004; A61M 2205/70
See application file for complete search history.

(56) References Cited

U.S. PATENT DOCUMENTS

| | | | | |
|---|---|---|---|---|
| 7,939,891 | B2 | 5/2011 | Matsuo et al. | |
| 9,415,187 | B2 | 8/2016 | Agnew | |
| 2002/0099327 | A1 | 7/2002 | Wilson et al. | |
| 2005/0059993 | A1* | 3/2005 | Ramzipoor ....... | A61M 25/0069 606/200 |
| 2005/0154250 | A1 | 7/2005 | Aboul-Hosn et al. | |
| 2008/0108969 | A1 | 5/2008 | Kerr | |
| 2010/0076406 | A1 | 3/2010 | Raulerson | |
| 2019/0255245 | A1* | 8/2019 | Kelly ................ | A61M 25/0026 |

* cited by examiner 120
122
190
128
127
132
136
50'
50
116

TRANSFORMABLE DUAL LUMEN CANNULA INTO A SINGLE LUMEN CANNULA AND METHODS OF USE

CROSS-REFERENCE TO RELATED APPLICATIONS

This Application claims priority to U.S. Provisional Patent Application 63/338,787, filed May 5, 2022, entitled "A TRANSFORMABLE DUAL LUMEN CANNULA INTO A SINGLE LUMEN CANNULA AND METHODS OF USE" and is a continuation in part of U.S. patent application Ser. No. 17/523,811, filed Nov. 10, 2021, entitled "DUAL LUMEN CANNULA AND METHODS OF USE" which claims priority to each of U.S. Provisional Patent Application 63/111,803, filed Nov. 10, 2020, and U.S. Provisional Patent Application 63/111,813, filed Nov. 11, 2020, the contents of each of which are incorporated by reference as if fully set forth herein.

FIELD OF THE INVENTION

This invention is directed to a dual lumen cannula assembly in general, and more specifically, this invention is directed to a dual lumen cannula in which the outer lumen and the inner lumen are connected within the body in real time and having opposite flow directions through a novel flow router connector. This invention is further directed to a transformable dual lumen cannula into a single lumen cannula, and vice versa, configured to allow subsequent low flow approach and high flow approach according to the patient's condition with the same cannula.

BACKGROUND OF THE INVENTION

Medical treatments that require extracorporeal treatment of blood, such as dialysis and extracorporeal oxygenation, require separate tubing for removal of untreated blood from the body and reinsertion of treated blood back into the body. There are two generally practiced techniques for implementing such tubing within the vascular system—two single lumen cannulas, and a dual lumen cannula. Both of these techniques have significant challenges.

Use of two single-lumen cannulas is disfavored because they require two separate incision sites. Use of multiple incision sites causes patient discomfort, especially for procedures in which the cannulas are retained within the body for hours or days, and also increases risk of infection. In addition, the medical team will need to repeat the insertion of the tubes twice, thus doubling the risk and the time required for this stage of the procedure.

Use of a dual lumen cannula is also challenging, for multiple reasons. One particular challenge of dual lumen cannulas relates to the manner in which the dual lumen cannulas are inserted and primed. Typically, a dual lumen cannula is inserted as a standalone device, with a distal end within the vascular system, and a proximal end outside the body. The proximal end includes two tubes, which may be branched in a Y-shape. With the dual lumen cannula fully inserted in the vein, each lumen of the proximal end of the dual lumen cannula is then connected to separate tubing. This connection process requires exertion of significant force on the dual lumen cannula, which raises the risk of puncturing of the blood vessel. In addition, it is necessary to exert care during the connection of each lumen to the tubing, to ensure that no air bubbles enter the vascular system. This is typically done by flushing saline in the open ends of each line. Despite the extensive training received by practitioners, it is still extremely difficult to prevent any air bubbles from entering the bloodstream. Entry of air bubbles may lead to formation of embolisms, which may be potentially fatal.

Some attempts were made in the art to use dual lumen cannulas. The following references may be considered as relevant to the field of the invention: US Patent Application No. 2021023336; U.S. Pat. Nos. 5,053,004; and 5,718,678.

SUMMARY OF THE INVENTION

In one main aspect, the present invention is aimed to provide a dual lumen cannula, composed of an outer lumen and an inner lumen separated thereof that are being assembled into a dual lumen cannula in real time, in vivo, upon insertion of the inner lumen into the outer lumen that is first being inserted into the patient's body in a simple standard procedure as a single lumen cannula. Both lumens are assembled within the patient's body by a novel connector assembly that further determines the flow direction in each of the lumens of the dual lumen cannula as will be described in detail below. The outer lumen and the inner lumen are preferably connected reversibly by the novel connector assembly that allows opposite flow directions within the outer and inner lumens of the dual lumen cannula while one cannula is being inserted within the other cannula.

In accordance with the present invention, the outer lumen cannula is being inserted to the patient's vascular system with minimal exertion of force on the cannula when it is positioned within the patient's vascular system as a single lumen cannula. The cannulation of the outer cannula is preferably performed by standard cannulation procedure.

When the outer lumen is positioned within the patient's body, the inner lumen is first being connected to a desired device or system, such as but not limited to, a blood treatment system, and being primed, such that it is ready to be inserted into the outer.

Thus, in one main aspect this invention is directed to a dual lumen cannula, the cannula comprising: at least one inner lumen having at least two ends, an inner lumen proximate end and an inner lumen distal end, a hollow intermediate extent between said two ends having one or more openings at the inner lumen distal end, and at least one inner lumen connector unit at the inner lumen proximate end; at least one outer lumen having at least two ends, an outer lumen proximate end and an outer lumen distal end, a hollow intermediate extent between said two ends having one or more openings, said intermediate extent further comprising one or more openings at the outer lumen distal end, and at least one outer lumen connector unit at the outer lumen proximate end; and at least one flow router; wherein the inner lumen is configured to be inserted into said outer lumen until said inner lumen connector unit is in coupling contact with said outer lumen connector unit. The flow router connects to the inner lumen connector unit, wherein the connection from the flow router to one or more medical devices is preferably but not necessarily collinear to the inner lumen and the outer lumen. In at least one embodiment, the flow router is collinear to the inner lumen and outer lumen on the machine side of a butterfly with suturing holes 116 when used. The intermediate extent of the inner lumen further includes one or more holes located between the distal end and the proximate end of the outer lumen, and within a region of the inner lumen which is within the outer lumen when assembled. The outer lumen preferably includes a narrow area at its distal end for centralizing the position of the inner lumen toward a target area. The openings on the intermediate extent of the outer lumen are at least one drainage opening.

Upon connection of the outer lumen connector unit to the inner lumen connector unit, the inner lumen connector unit provides a flow path from the flow router to both said outer lumen and said inner lumen. The flow router further includes an inlet port for connecting to one or more connector tubing connected to at least one medical device.

The outer lumen may further include at least one suturing element that allows fixating the outer cannula to the patient's body once it is cannulated and may further include one or more calibration marks.

The flow router of the dual lumen cannula provided herein, may further include a first internal flow channel position connection area from the outer cannula through the outer lumen connector unit then inner lumen connector unit to the medical device. In some other embodiments, the flow router further includes a second internal flow channel from the medical device through the inner lumen connector unit to the inner lumen.

Yet, in some other embodiments of the invention, the blood flow is reversed such that the first internal flow channel provides a flow path from the medical device through the inner lumen connector unit to the outer lumen connector unit, then to the outer lumen.

Alternatively, the blood flow is reversed such that the second internal flow channel provides a flow path from the inner cannula through the inner lumen connector unit to the medical device.

In some optional embodiments, the outer lumen connector unit further includes one or more barbs. Optionally, the outer lumen and the outer lumen connector unit may be formed as a single piece.

In some optional embodiments, the inner lumen connector unit further includes one or more flexible connectors for connecting and sealing to one or more barbs from the outer lumen connector unit.

In some optional embodiments, the inner lumen connector unit further includes a vertical separating wall and chambers for creating a separate flow channel via one or more lumen opening to the inner lumen and a separate flow channel to the outer lumen through the outer lumen connector unit.

This invention is further directed to a process for introducing a cannula to a patient vascular system, the process comprising at least the following steps: inserting a first outer lumen cannula into a patient's vascular system through use of an introducer, and optionally a guide wire, drawn through the outer lumen up to its distal end; withdrawing the introducer and guidewire causing a small vacuum to form in the outer lumen, which is back filled with blood; priming a second inner lumen cannula through use of a priming cap connected to a priming system, whereupon following completion of the priming, the priming cap is removed; and inserting the second inner lumen cannulas within said first outer lumen cannula until inner lumen connection unit fastens to an outer lumen connection unit.

The said first outer lumen cannula may be sutured to the skin of the patient by stitching regular sutures through butterfly. Optionally, the one or more flow router is connected to the inner lumen connection unit, and the medical device is connected to the flow router.

In one another aspect, the present invention is aimed to provide a transformable dual lumen cannula, which can be used in low flow extracorporeal oxygenation system and be transformed in real time into a single lumen cannula where the medical condition of the patient requires high flow extracorporeal oxygenation approach. The transformation of the dual lumen cannula into a single lumen cannula and vice versa is simple and fast, intuitive and friendly both, to the patient and the medical team.

In yet, one another main aspect of the invention, a single lumen cannula for extracorporeal blood oxygenation may be transformed while already being within the patient's body into a dual lumen cannula when the patient's medical condition is being improved and high flow ECMO is not needed any longer as low flow oxygenation may be sufficient to support its lungs.

BRIEF DESCRIPTION OF THE DRAWINGS

Examples illustrative of embodiments of the disclosure are described below with reference to figures attached hereto. Dimensions of components and features shown in the figures are generally chosen for convenience and clarity of presentation and are not necessarily shown to scale. Many of the figures presented are in the form of schematic illustrations and, as such, certain elements may be drawn greatly simplified or not-to-scale, for illustrative clarity. The figures are not intended to be production drawings.

The figures (Figs.) are listed below.

FIG. 7C is a schematic cross-section side view of the dual lumen cannula of FIG. 7A according to optional embodiments of the invention.

FIG. 7D is a schematic illustration of the cross-section side view of FIG. 7B, wherein the drainage outer lumen and an infusion inner lumen are partially detached from one another according to optional embodiments of the invention.

FIGS. 10A-10B are schematic isometric views of the transformable dual lumen cannula in a single lumen form, wherein FIG. 10A illustrates the drainage outer lumen ready to be connected to a single lumen connector; and FIG. 10B illustrated the drainage outer lumen connected to the single lumen connector ready to be used in a single lumen cannula form, in accordance with some optional embodiments of the invention.

FIG. 10C is a schematic cross section view of the transformable dual lumen cannula in a single lumen cannula form connected to the single lumen connector as illustrated in FIG. 10B, in accordance with some optional embodiments of the invention.

DETAILED DESCRIPTION OF EMBODIMENTS OF THE INVENTION

Figure 1A:
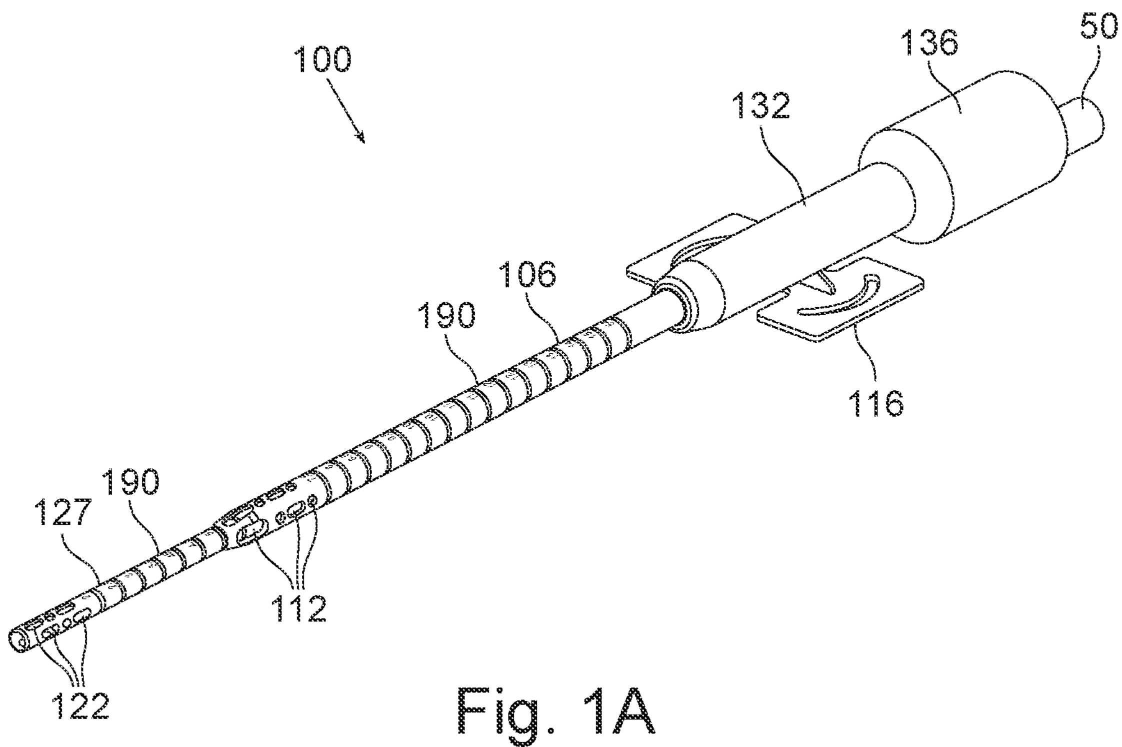
FIG. 1A is an isometric view of at least one embodiment of the inventive dual lumen cannula in an assembled, ready to use form comprising a drainage outer lumen and an infusion inner lumen connected therethrough by a connector assembly according to optional embodiments of the invention.

The inventors of this application have developed a unique dual lumen cannula, composed of an outer lumen and an inner lumen separated thereof that are being assembled into a dual lumen cannula in real time, in vivo, upon insertion of the inner lumen into the outer lumen that is first being inserted into the patient's body in a simple standard procedure as a single lumen cannula. Both lumens are assembled within the patient's body by a novel connector assembly that further determines the flow direction in each of the lumens of the dual lumen cannula as will be described in detail below. The outer lumen and the inner lumen are preferably connected reversibly by the novel connector assembly that allows opposite flow directions within the outer and inner lumens of the dual lumen cannula while one cannula is being inserted within the other cannula. The inventors of this application further developed a unique extracorporeal blood oxygenation system in low flow rates of up to 30 ml/Kg per minute. The novel extracorporeal oxygenation system of the inventors is preferably used for acute respiratory failure patients treated with noninvasive ventilation as they still exhibit spontaneous breathing and uses a blood circulation rate of no more than 30 ml/kg per minute. This circulation rate is much lower than the circulation rate used in ECMO that ranges between 60-80 ml/kg/min for V-V (veno-venous) ECMO and 50-60 ml/kg/min for V-A (veno-arterial) ECMO. The inventors of this application have come to the surprising understanding that reduced volume circulation of the patient's blood and oxygenation of only a portion of the blood, and not its entire volume or most of the volume, can improve respiration of conscious patients that are still capable of spontaneous breathing, reduce discomfort and minimize the risk of complications. The novel system disclosed in PCT/IL2021/051431 and incorporated herein in its entirety by reference, is designed to support a functioning (yet sick) lung(s), and to work in tandem with a patient who is awake and breading on his/her own accord, albeit at a reduces capacity. That extracorporeal oxygenation system is aimed to supplement the oxygen in the blood, which is insufficient due to an underperforming lung. This is a major point of difference in acute respiratory care, as in contrast to ECMO that requires the lung being "shut down" and therefore requires the entire replacement of lung functionality, the extracorporeal blood oxygenation system and methods disclosed in PCT/IL2021/0514 allows the lung to be left alone and treated by the medical team, instead of overburdening it with Mechanical Ventilation.

However, in some cases, patients not considered candidates for ECMO, may in the future, be treated with low flow approach. Nonetheless, patient may continue to deteriorate albeit low flow ECMO treatment. In such a scenario the patient might become candidate for ECMO treatment utilizing the entire cardiac output, and the cannula currently used for the low flow treatment cannot be utilized for high flow (e.g. 5-8 liters per minute).

The present invention addresses such a potential clinical scenario. The current invention is aimed to allow physician to use a dual lumen cannula in a low flow approach and transform the very same cannula into a single lumen cannula such that another single lumen cannula can be introduced in order to allow for an ECMO treatment utilizing the entire patients' cardiac output (high flow approach).

The novel transformable dual lumen cannula into a single lumen cannula and vice versa may further support the opposite scenario, where the patient is first being treated by high flow approach (connected to ECMO system) and then, during the recovery process the high flow approach is being replaced by low flow approach (connected to a low flow extracorporeal oxygenation system as mentioned in the above), and the very same single tumen cannula is transformed into a dual lumen cannula, sparing the need to re-cannulate the patient. In the following description, various aspects of the novel single dual lumen cannula and flow router connector will be described. For the purpose of explanation, specific configurations and details are set forth in order to provide a thorough understanding of the invention.

Although various features of the disclosure may be described in the context of a single embodiment, the features may also be provided separately or in any suitable combination. Conversely, although the disclosure may be described herein in the context of separate embodiments for clarity, the disclosure may also be implemented in a single embodiment. Furthermore, it should be understood that the disclosure can be carried out or practiced in various ways, and that the disclosure can be implemented in embodiments other than the exemplary ones described herein below. The descriptions, examples and materials presented in the description, as well as in the claims, should not be construed as limiting, but rather as illustrative.

In one main aspect, the present invention is aimed to provide a convenient and safe solution that allows practitioners to insert a dual lumen cannula as simple and safe as inserting a single lumen cannula. Beside the simplicity of inserting the cannula into the target area and advantage to the medical team, the novel solution is also beneficial to the patient as it allows to thread the second lumen through the first lumen in vivo, one into the other, after insertion of the first single lumen, without the need to create an additional incision at the entrance area as required when regular dual lumen cannula is used, and save the patient inconvenient that may occur, possible contamination and additional scar. Both lumens are connected in vivo by a proprietary novel connector assembly that is configured to connect the two lumens and further to route the opposite flows at the inner lumen and the outer lumen. Thus, the outer lumen is inserted into the vascular system of a patient, and the inner lumen is inserted through the outer lumen to a desired location.

As used herein, the term “cannula” refers to a thin tube inserted into a blood vessel that permits extraction or infusion of blood therethrough from/into the blood vessel. A “dual lumen cannula”, in the disclosed embodiments, is a cannula that includes an inner lumen enveloped by an external lumen, thus enabling simultaneous, physically separated inflow and outflow of blood via a single dual lumen cannula inserted into the patient vascular system.

The term “proximal” refers to a direction closer to the blood treatment system or any other machine to which the dual lumen cannula is connected, and the term “distal” refers to a direction toward or within the patient body/vascular system.

The term “lumen” refers to the inner spaces in tubes for the transport of liquids or gases.

The term “drainage lumen” or “outer lumen” refers to the lumen that is responsible for draining or transporting the blood from the body of a subject into a machine before treatment. In the below description the terms “outer lumen”, “outer cannula”, “outer drainage cannula”, “drainage cannula” and “drainage lumen” are all used interchangeably and directed to the same component.

The term “infusion lumen” or “inner lumen” refers to the lumen that infuses the blood back to the body from the machine after the treatment. In the below description the terms “inner lumen”, “inner cannula”, “inner infusion cannula”, “infusion cannula” and “infusion lumen” are all used interchangeably and directed to the same component. The term “transformable cannula” as used herein refers to a dual lumen cannula that can be converted to be used as a single lumen cannula, and a single lumen cannula that can be transformed to be used as a dual lumen cannula, both transformations performed while the cannula is positioned within the patient’s body.

Although the description herein refers to the outer lumen as a drainage lumen and to the inner lumen as the infusion lumen, in some other optional embodiments and implementation of the present invention the outer lumen may be used to infuse blood toward the body and the inner lumen may be used to drain blood out from the body.

Additionally, although reference is made to drainage and infusion of blood, it should be clear that other body fluids may also be drained and infused by the novel dual lumen cannula provided herein and the present invention is not limited in any way to blood.

Reference is now made to the drawings:

FIG. 1A is a schematic isometric view illustration of dual lumen cannula 100 of the invention in an assembled, ready to use form. In this form, the dual lumen cannula 100 includes a drainage outer lumen configured to drain blood through drainage openings 112 of cannula 106 from the body of a treated patient toward an extracorporeal machine for treating the drained blood, and an infusion inner lumen configured to infuse blood through infusion opening 122 of cannula 127 from the extracorporeal machine back into the body of the treated patient, the inner and outer lumens are connected to each other by a connector assembly that connect the two lumens and route the blood flow in each of them as will be described in details below.

Cannula 106 of the outer lumen may include calibration marks 190 to thereby provide the medical team indication about the penetration length. In a similar manner, cannula 127 of the inner lumen may also contain calibration marks 190 to monitor the penetration length of the inner lumen.

The inner lumen includes a connector unit 132 that is preferably but not necessarily, an integral part of the inner lumen. Optionally, connector unit 132 is connected to a butterfly with suturing holes 116 that may be fixed to a patient’s skin with standard sutures, to stabilize the position of the dual lumen cannula during the medical treatment. It should be clear that other means to stabilize and fasten the cannula to the patient’s body may be used and butterfly 116 is only one none-limiting exemplary implementation.

Connector unit 132 of the inner lumen is functionally connected at its proximal end to a connector unit 136 also referred hereinafter as “flow router” 136. Flow router 136 is the connecting unit between the dual lumen cannula and the extracorporeal machine, and it is configured and operable to set the blood flow in opposite directions between the inner and outer lumens and preferable from a flow at two separated parallel tubes into a flow within two insertable one into the other lumens. Connector unit 132 is further connected to a connecting configuration of cannula 106 as will be described with reference to FIGS. 1C-1D hereinbelow. The connection between the inner lumen and the outer lumen is performed in vivo, within the patient’s body, as the outer lumen is first inserted into the patient as a single lumen cannula and only afterward, the inner lumen is threaded into the outer lumen until they are coupled into a dual lumen cannula. Also shown in this drawing tube connection platform 50 that is one of two tube connector platforms that are connected to flow router 136 and allow the connection of the dual lumen cannula of the invention to tubes for transporting blood from the patient's body toward the extracorporeal machine and for transporting blood on the opposite direction, from the extracorporeal machine towards the patient's body.

Figure 1B:
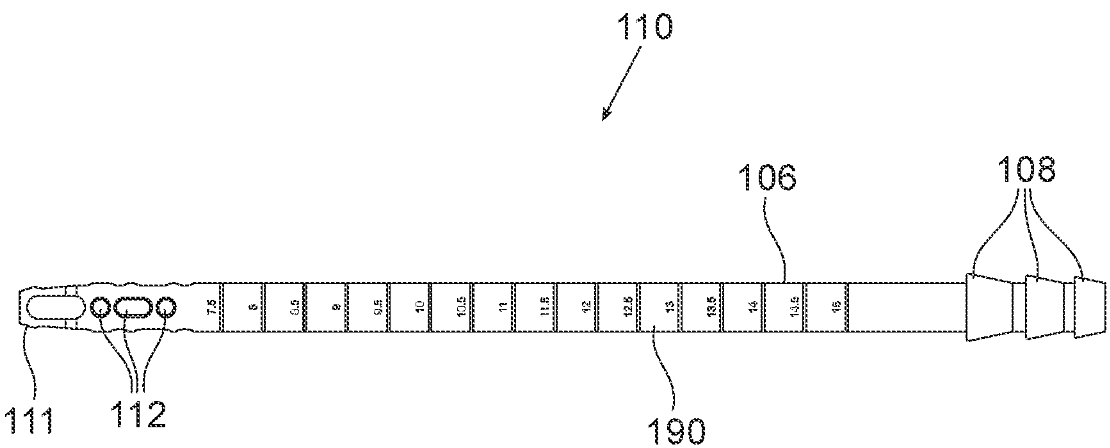
FIG. 1B is a schematic side view of at least one embodiment of the drainage outer lumen of the dual lumen cannula of FIG. 1A in accordance with some optional embodiments of the invention.

FIG. 1B is a schematic side view of the drainage outer lumen 110 of the dual lumen cannula of FIG. 1A in accordance with some optional embodiments of the invention. In this embodiment, outer lumen 110 includes at least a cannula 106, also denoted interchangeably "inner cannula" and "infusion cannula", having a diameter that is larger than the diameter of the inner lumen 120 to thereby allow the insertion of inner lumen 120 through it. Cannula 106 has a narrow area 111 at its distal end mainly for centralizing the position of the inner lumen toward the target area, and at least one drainage opening 112. Optionally, cannula 106 contain calibration marks on it that may further be marked with numbers 190 to indicate the penetration length of outer lumen 110 into the patient's body. Cannula 106 includes at its proximal end a connector unit 108. In the specific example illustrated herein, connector unit 108 is made of subsequent barbs that are continuous to cannula 106. Upon connection of the inner lumen to the outer lumen connector unit 108 is configured to be inserted to a complementary niche or socket at inner lumen connector unit as will be described with reference to FIGS. 1C-1D. Other connecting solutions such as Luer lock, snap connection, and the like can be used alternatively.

Figures 1C, 1D, 1E:
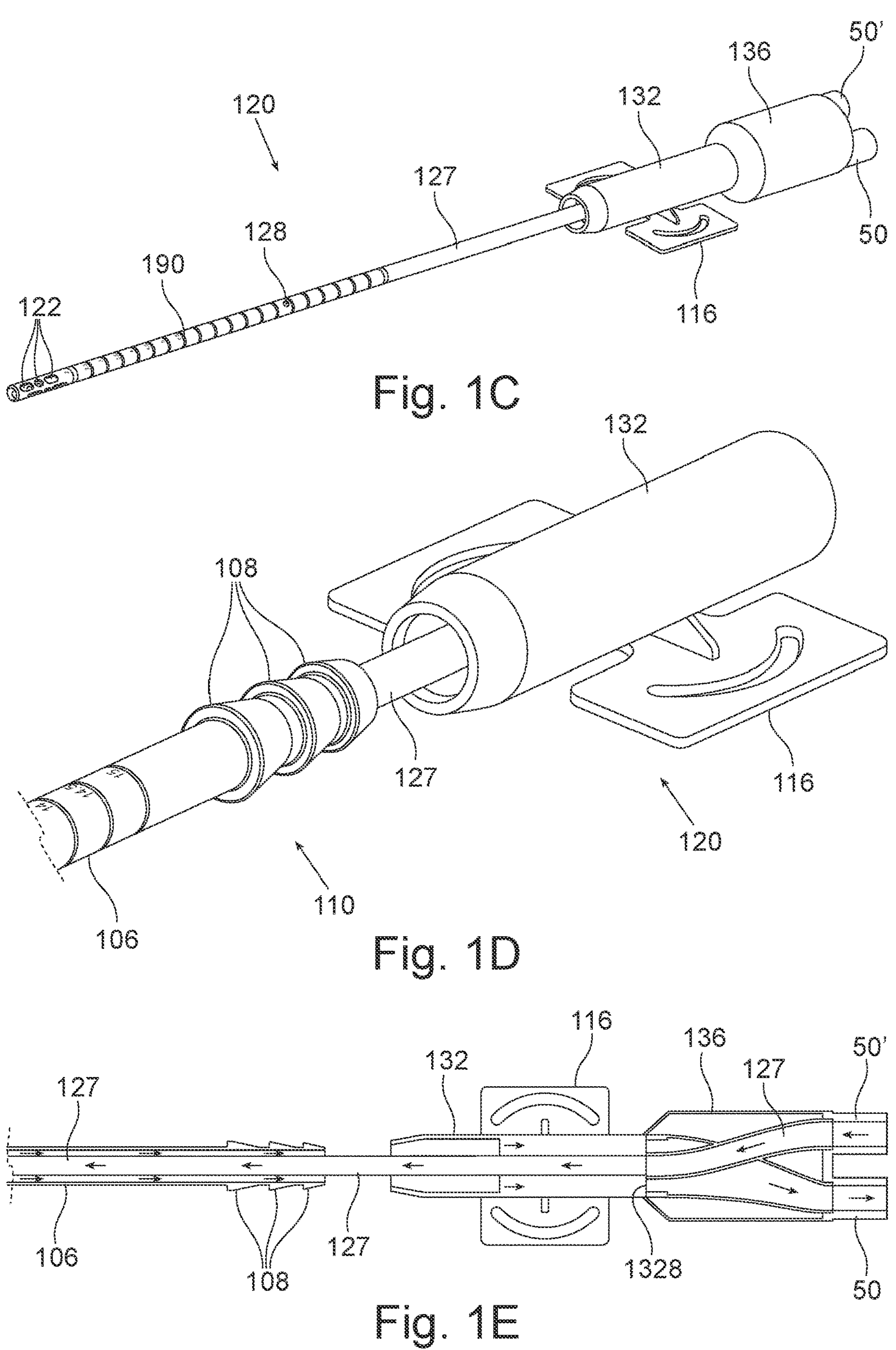
FIG. 1C is a schematic isometric view of at least one embodiment of the infusion inner lumen of the dual lumen cannula of FIG. 1A in accordance with some optional embodiments of the invention.
FIG. 1D is a schematic isometric partial view illustrations of the connection area between the inner lumen and the outer lumen of the dual lumen cannula of FIG. 1A according to some optional embodiments of the invention.
FIG. 1E is a schematic cross section partial view of the connection area between the inner lumen and the outer lumen of the dual lumen cannula of FIG. 1A including the flow router connector, according to some optional embodiments of the invention.

FIG. 1C is a schematic isometric view of an infusion inner lumen 120 of the dual lumen cannula of FIG. 1A in accordance with some optional embodiments of the invention. Inner lumen cannula 120 includes cannula 127, inner lumen connector unit 132 that in the example illustrated herein is attached to flow router 136 and connected as one piece to the proximal end of cannula 127. Cannula 127 has smaller diameter relative to cannula 106 that functionally allow inserting it through cannula 106 and bigger length that allow it to extend beyond cannula 106 to the target area. Cannula 127 includes at least one infusion opening 122 at its distal end that allow to return treated blood from the extracorporeal machine back to the patient's vascular system. Cannula 127 may further include a pressure regulation hole 128 that is formed along the perimeter of the inner lumen. Pressure regulation hole 128 is located at a location along cannula 127 such that, when inner lumen 120 is inserted into outer lumen 110, pressure regulation hole 128 is covered by outer lumen 110. Pressure regulation hole 128 functions to alleviate high pressure situations in the infusion lumen, which may lead to cavitation. Cavitation is a phenomenon in which rapid changes of pressure in a liquid lead to formation of small vapor-filled cavities in places where the pressure is relatively low. Cavitation in blood vessels may cause the formation of liquid jets, and potentially may cause vessel rupture. The dimensioned of hole 128 is determined such that when pressure in the inner lumen 120 increases beyond a predetermined level, the blood passes through the pressure regulation hole 128 from the inner lumen to the outer lumen, thereby bypassing the patient vascular system. In such circumstances, blood flows into hole 128 based on the principle of fluid dynamics that a liquid always flows along a path of least resistance. The blood continues to flow through hole 128 until the pressure in the infusion lumen 120 decreases, to the point that the infusion lumen 120 again becomes the path of least resistance. Connector unit 132 may include a butterfly with suture holes 116 to allow stitching the dual lumen cannula of the invention to the patient's skin during the medical process.

Also shown in this views, tubes connection platforms 50 and 50' that allow connecting outer tubes to the inner lumen and to the outer lumen to flow the drained blood into the machine, and from the machine to flow the blood back to the patient's vascular system respectively. Inner lumen 120 may further include at its distal end a priming cap (not shown). The priming cap is removable and may be connected to a priming system for priming inner lumen 120. For example, the priming cap may be connected to a source of saline and may be removed after priming is completed.

Proximal to priming cap, inner lumen 120 includes infusion openings 122 for fluidic connection to the patient's vascular system. These openings form a gateway for treated blood to flow back into the cardiovascular system. Also shown in these drawings, calibration marks 190 and tubes 50 and 50' that transport the blood into and from the medical machine.

FIG. 1D is a schematic isometric partial view illustration of the connection area between inner lumen 120 and the outer lumen 110 of the dual lumen cannula 100 of FIG. 1A according to some optional embodiments of the invention. In this view, cannula 127 is connected at its proximal end to inner lumen connector unit 132 and is being inserted through its distal end into the proximal end of cannula 106 through outer connector unit 108. Connector unit 108 is then being pushed into the inner space of inner lumen connector unit 132, such that its barbs are hooked and covered by connector unit 132.

FIG. 1E is a schematic cross section partial view of the connection area between the inner lumen 120 and the outer lumen 110 of the dual lumen cannula 100 of FIG. 1A including the flow router connector, according to some optional embodiments of the invention.

In the cross section partial view, the opposite flow directions of the drained blood and the infused blood within infusion inner cannula 127 and drainage outer cannula 106 is illustrated. For simplicity of explanation, connector unit 108 of outer lumen cannula and connector unit 132 of inner lumen cannula are separated to clearly demonstrate the parts related to the connection. The blood flow begins only when the two cannulas are coupled and when barbs 108 are pushed inside connector unit 132 distal end that hook it within it. During the coupling of the two lumens, cannula 106 embracing cannula 127 that is inserted into it. The blood flow in both lumens as well as in connector units 131 and 132 is performed in parallel lumens and in opposite directions as indicated by the arrows along the two cannulas. Flow router 136 gathers all the drained blood that flows in chambers 1326 together into one tube that will be connected to tube connector platform 50 to transport the blood into the extracorporeal machine for treatment. In the same manner but in the opposite direction, treated blood from the extracorporeal machine is infused back into the vascular system of the treated patients through a tube that will be connected to tube connector platform 50' to transports the treated blood through flow router 136 into cannula 127 toward the patient's body.

Figures 2A, 2B:
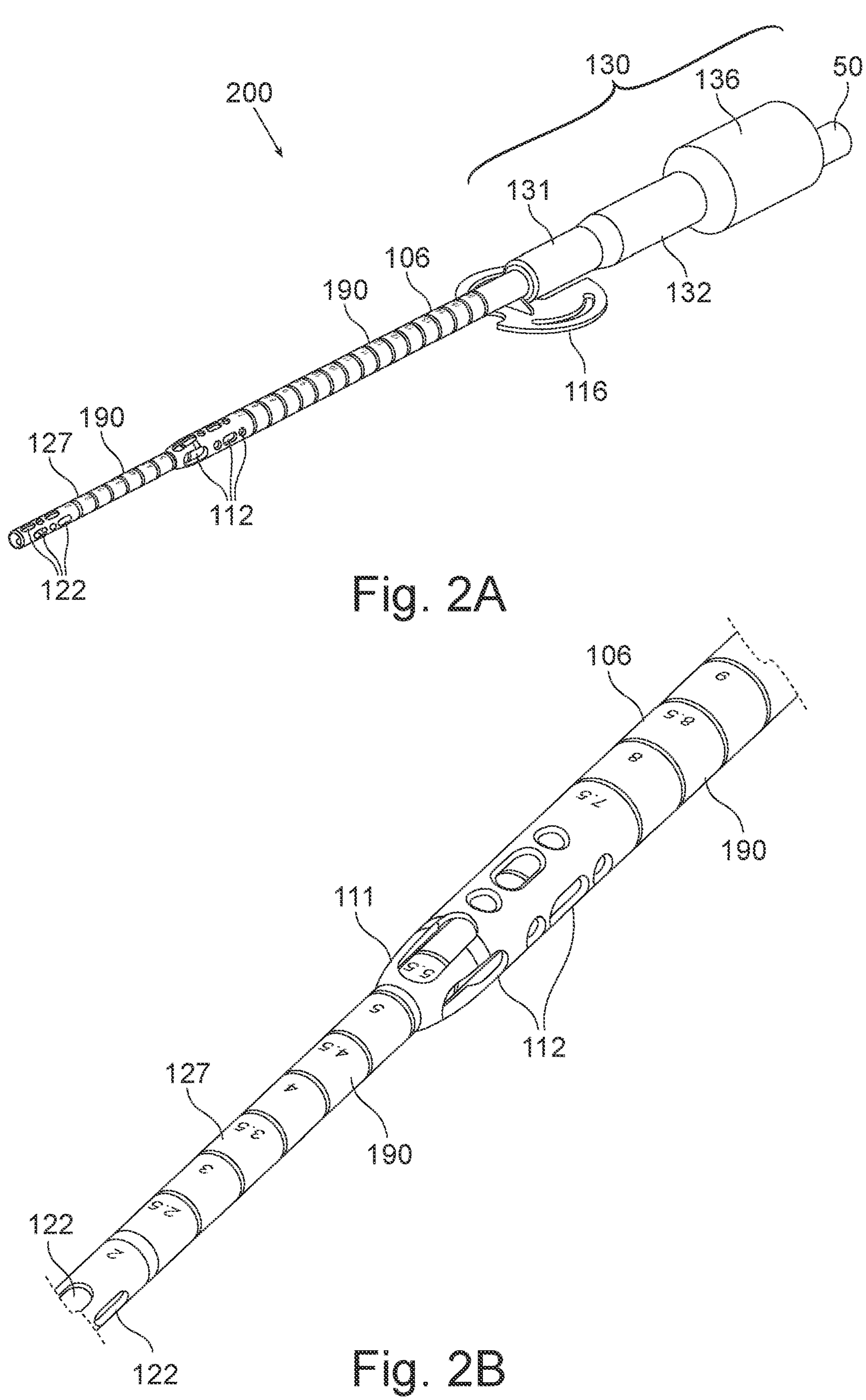
FIG. 2A is an isometric view of at least one another embodiment of the inventive dual lumen cannula in an assembled, ready to use form comprising a drainage outer lumen and an infusion inner lumen connected therethrough by a connector assembly according to optional embodiments of the invention.
FIG. 2B is a schematic isometric close up view illustration of the overlapping area at the distal end of the outer drainage cannula and the extended inner infusion cannula out from the outer cannula of dual lumen cannula of FIG. 2A.

FIG. 2A is a schematic isometric view illustration of dual lumen cannula 200 of the invention in an assembled, ready to use form. In this form, the dual lumen cannula 200 includes a drainage outer lumen comprising cannula 106 configured to drain blood through drainage openings 112 from the body of a treated patient toward a machine for treating the drained blood, and an infusion inner lumen comprising cannula 127 configured to infuse blood through infusion opening 122 from the machine back into the body of the treated patient, the inner and outer lumens are connected to each other by a connector assembly that connect the two lumens and route the blood flow in each of them as will be described in details below.

Optionally, cannulas 106 and 127 include calibration marks 190 to thereby provide the medical team indication about the penetration length. The outer lumen includes at its proximal end outer connector unit 131 that is preferably but not necessarily an integral part of a connector assembly 130 and configured to allow the physical connection of the outer lumen with the inner lumen. The outer lumen may optionally contain a butterfly with suturing holes 116 that may be fixed to a patient's skin with standard sutures, to allow fixation of the outer cannula to the patient's body so as to stabilize its position before insertion of the inner cannula through it. In this specific example, connecter unit 131 is connecter to butterfly 116. It should be clear that other means to stabilize and fasten the outer cannula to the patient's body are also within the scope of this invention and the example provided herein is only one exemplary optional implementation.

Also shown in this drawing inner lumen connector unit 132 that is preferably but not necessarily, an integral part of the inner lumen. Upon threading the inner lumen into the outer lumen, outer lumen connector unit 131 and inner lumen connector unit 132 are coupled as will be described in detail with reference to FIGS. 5A-5B. Also shown in this drawing flow router 136. Flow router 136 is the connecting unit between the dual lumen cannula and the extracorporeal machine, and it is configured and operable to set the blood flow in opposite directions between the inner and outer lumens. Connector units 131, 132, and 136 compose together connector assembly 130. Also shown in this drawing tube connector platform 50 that has the same role as described with reference to FIG. 1A above.

FIG. 2B is a schematic isometric close up view illustration of the overlapping area at the distal end of the outer drainage cannula 106 and the inner infusion cannula 127 extended out from the tip of the distal portion of outer cannula 106 of the dual lumen cannula of FIG. 2A. As shown in this drawing, the distal tip of outer cannula 106 is narrow relative to the diameter of the outer lumen dimensions at other areas. This narrow area 111 at the distal end of outer cannula 106 forces centralization of inner cannula 127 when it passes through it toward the target area within the patient's body. Inner cannula 127 is preferably longer than outer cannula 106 in a manner that allows infusing the treated blood through infusion openings 122 away from the drained blood through drainage openings 112. The distance that the inner cannula 127 extends beyond outer cannula 106 is preferably a fixed length. Also shown in this drawing are calibration marks 190 on both outer cannula 106 and inner cannula 127. The calibration marks are optional features only and other methods to estimate the penetration length may be used. Also shown in this drawing pressure regulation hole 128 positioned on inner lumen 120.

Figure 3A:
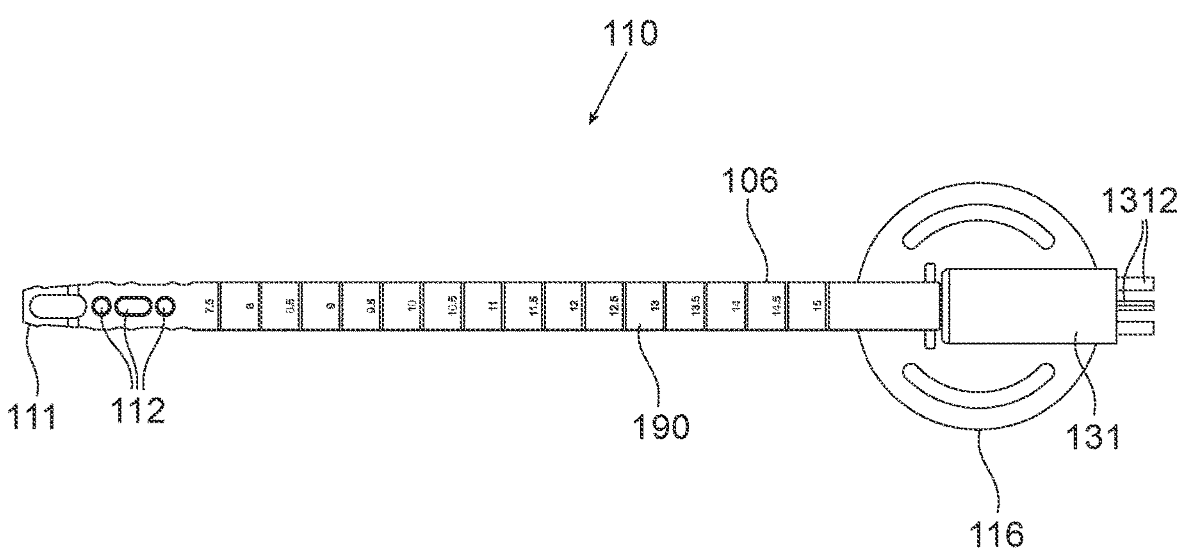
FIGS. 3A-3B are schematic top view and isometric view illustrations respectively of the drainage outer lumen of dual lumen cannula of FIG. 2A in accordance with some optional embodiments of the invention.
Figure 3B:
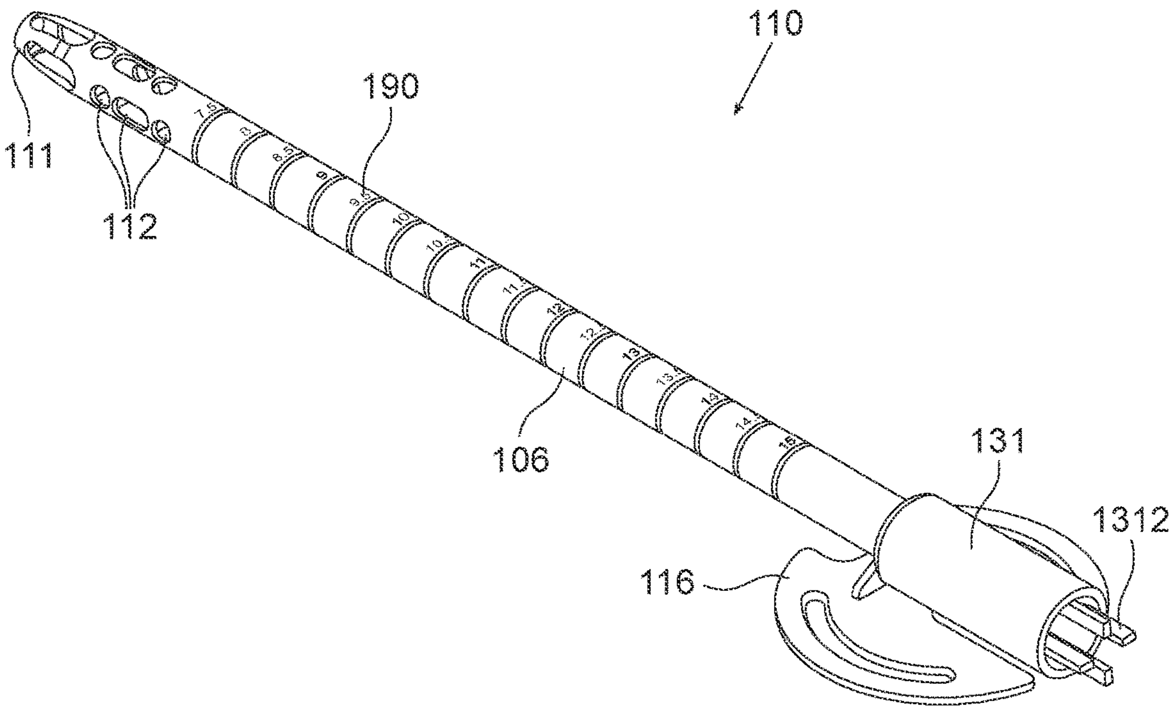

FIGS. 3A-3B are schematic top view and isometric view illustrations respectively of the drainage outer lumen 110 of dual lumen cannula 200 of FIG. 2A in accordance with some optional embodiments of the invention. Outer lumen 110 includes at least a cannula 106 having a fixed diameter that is larger than the diameter of the inner lumen 120 to thereby allow the insertion of inner lumen 120 through it. Cannula 106 has a narrow area 111 at its distal end mainly for centralizing the position of the inner lumen toward the target area, and at least one drainage opening 112. Optionally, cannula 106 contains calibration marks on it that may further be marked with numbers to indicate the penetration length of outer lumen 110 into the patient's body. Cannula 106 is attached at its proximal end to outer connector unit 131 that includes in the specific example illustrated herein at least two protruding elements 1312 configured to be inserted to a complementary niche or socket at inner lumen connector unit 132 of inner lumen 120. Other connecting solutions such as Luer lock, barbs, snap connection, or else can be used alternatively. In some optional embodiments, outer lumen 110 further include a suturing element that allows to fixate outer cannula 110 to the patient's body once it is cannulated, to ensure minimal movement and undesired pulling of the cannula from the patient's body. Fixation of the outer drainage cannula to the body before insertion of the inner cannula through it, further ensure stable drainage and infusion of the blood from the patient's body and back into it.

Figure 4A:
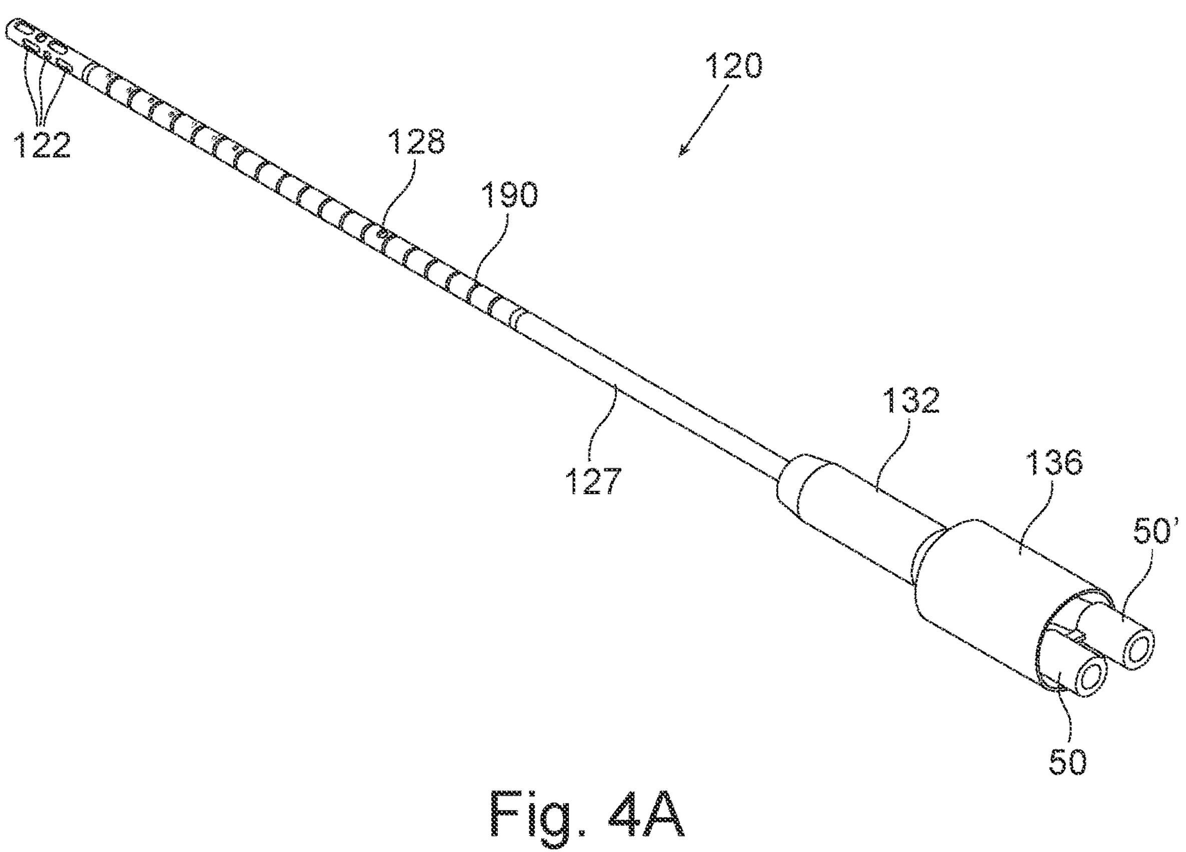
FIGS. 4A-4B are schematic isometric back view and isometric side view illustrations of the infusion inner lumen of the dual lumen cannula of FIG. 2A in accordance with some optional embodiments of the invention.
Figure 4B:
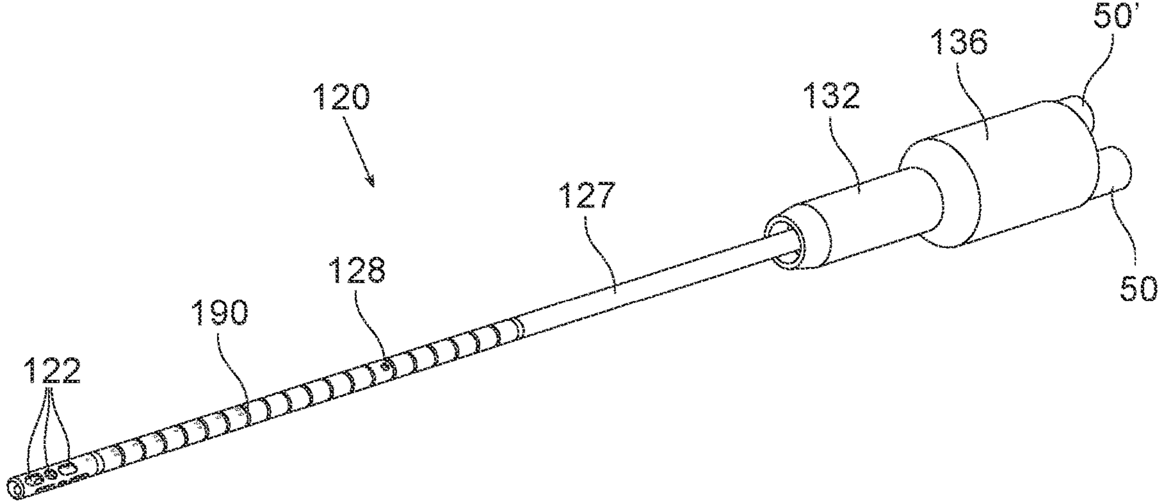

FIGS. 4A-4B are schematic isometric back view and isometric side view illustrations of infusion inner lumen 120 of dual lumen cannula 200 of FIG. 2A in accordance with optional embodiments of the invention. In these drawings, inner lumen connector unit 132 and flow router 136 are attached to each other and connected as one piece to the proximal end of cannula 127. Cannula 127 has smaller diameter relative to cannula 106 that functionally allow inserting it through cannula 106 and bigger length that allow it to extend beyond cannula 106 to the target area. Cannula 127 includes at least one infusion opening 122 at its distal end that allow to return treated blood from the extracorporeal machine back to the patient's vascular system. Cannula 127 further includes pressure regulation hole 128 that is formed along the perimeter of the inner lumen. Pressure regulation hole 128 is located at a location along cannula 127 such that, when inner lumen 120 is inserted into outer lumen 110, pressure regulation hole 128 is covered by outer lumen 110. Pressure regulation hole 128 functions to alleviate high pressure situations in the infusion lumen, which may lead to cavitation. Cavitation is a phenomenon in which rapid changes of pressure in a liquid lead to formation of small vapor-filled cavities in places where the pressure is relatively low. Cavitation in blood vessels may cause the formation of liquid jets, and potentially may cause vessel rupture. The dimensioned of hole 128 is determined such that when pressure in the inner lumen 120 increases beyond a predetermined level, the blood passes through the pressure regulation hole 128 from the inner lumen to the outer lumen, thereby bypassing the patient vascular system. In such circumstances, blood flows into hole 128 based on the principle of fluid dynamics that a liquid always flows along a path of least resistance. The blood continues to flow through hole 128 until the pressure in the infusion lumen 120 decreases, to the point that the infusion lumen 120 again becomes the path of least resistance.

Also shown in these views, tubes connector platforms 50 and 50' that allows connecting the extensions of the inner lumen and the outer lumen to tubes for transporting the drained blood into the machine, and from the machine back to the patient's vascular system. Inner lumen 120 may further include at its distal end a priming cap (not shown). The priming cap is removable and may be connected to a priming system for priming inner lumen 120. For example, the priming cap may be connected to a source of saline and may be removed after priming is completed.

Proximal to priming cap, inner lumen 120 includes infusion openings 122 for fluidic connection to the patient's vascular system. These openings form a gateway for treated blood to flow back into the cardiovascular system. Also shown in these drawings, calibration marks 190 and tube connector platforms 50 and 50' for transporting the blood into and from the medical machine.

Figure 5A:
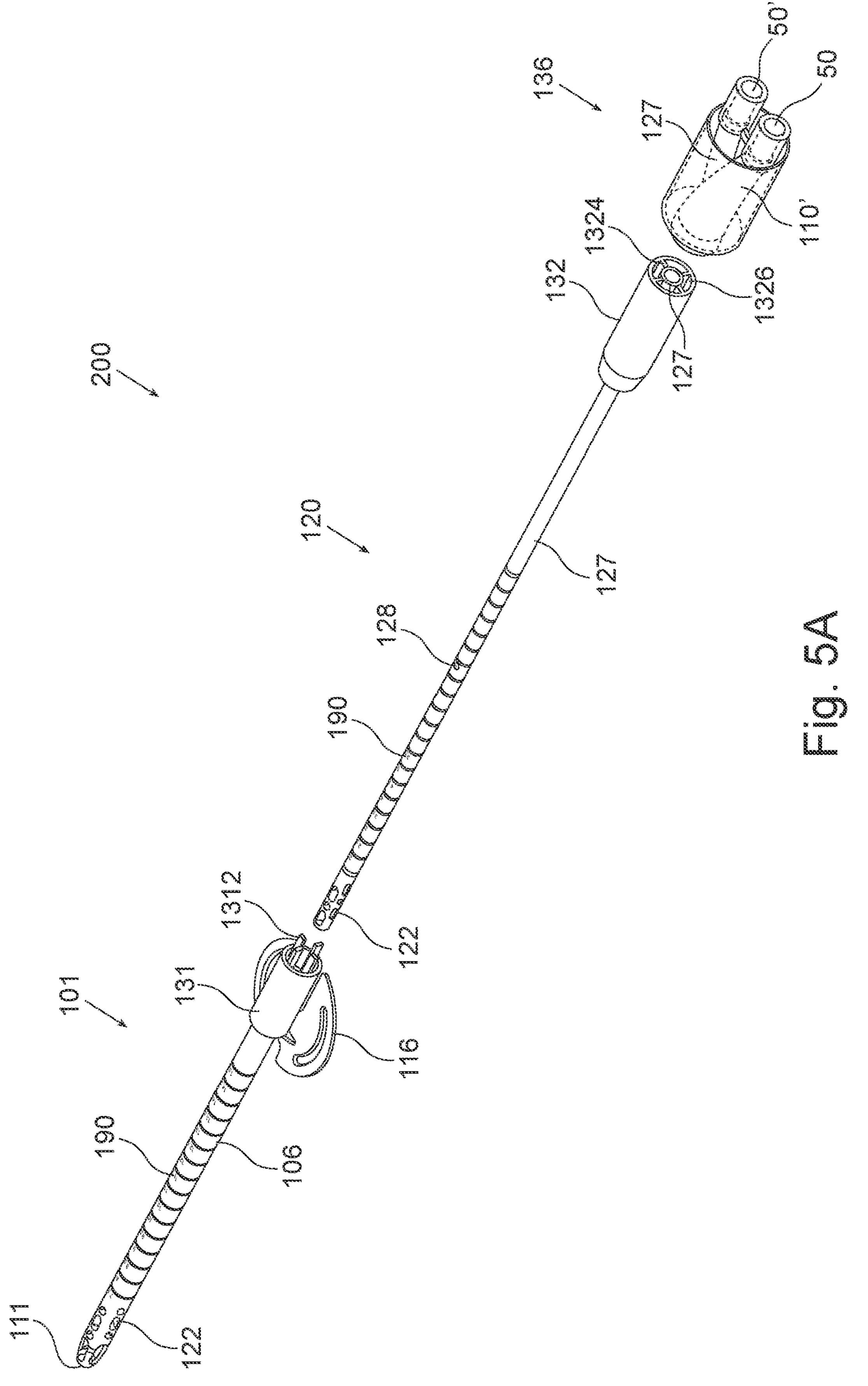
FIG. 5A is a schematic exploded view illustration of the dual lumen cannula of FIG. 2A illustrating major components of the dual lumen cannula of the invention.

FIG. 5A is a schematic exploded view illustration of the dual lumen cannula 200 of FIG. 2A illustrating the major components of the device. As shown in this drawing dual lumen cannula 200 is composed of three main functional components: the outer lumen 110, the inner lumen 120 and the flow router 136 that include at its proximal end tube connection platforms 50 and 50' to thereby allow transport of the blood into and from the medical machine.

In some preferred embodiments of the invention, flow router 136 is an integral part of inner lumen connector unit 132 and both are connected as one unit to the external end of a lumen so as to create inner lumen 120. As shown in this view, inner lumen together with inner lumen connector unit 132 and optionally further with connector unit 136 are designed to be threaded through outer lumen 110 that is pre cannulated as a single lumen cannula into the patient's body. Also shown in this drawing the connectors units with the connecting elements between the three connector units. These elements will be described in detail hereinafter. However, the connecting elements described herein should be construed as one non limiting implementation of the invention as other connecting means are also optional embodiments that may be implemented to connect between the connector assembly units of the invention. The following elements are also shown in this view:

For outer lumen cannula 110: outer connector unit 131, protruding elements 1312, cannula 106, calibration marks 190, drainage openings 112, narrow area of outer cannula 111, and butterfly with suturing holes 116.

For inner lumen cannula 120: inner lumen connector unit 132, cannula 127, calibration marks 190, infusion openings 122, Pressure regulation hole 128, vertical separating wall 1324, and chambers 1326.

For flow router 136: chamber 110', cannula 127. Also shown tubes 50 and 50' that are not part of flow router 136 but rather connected to its openings.

Detailed description of all components and their functional role is described hereinbelow.

Figure 5B:
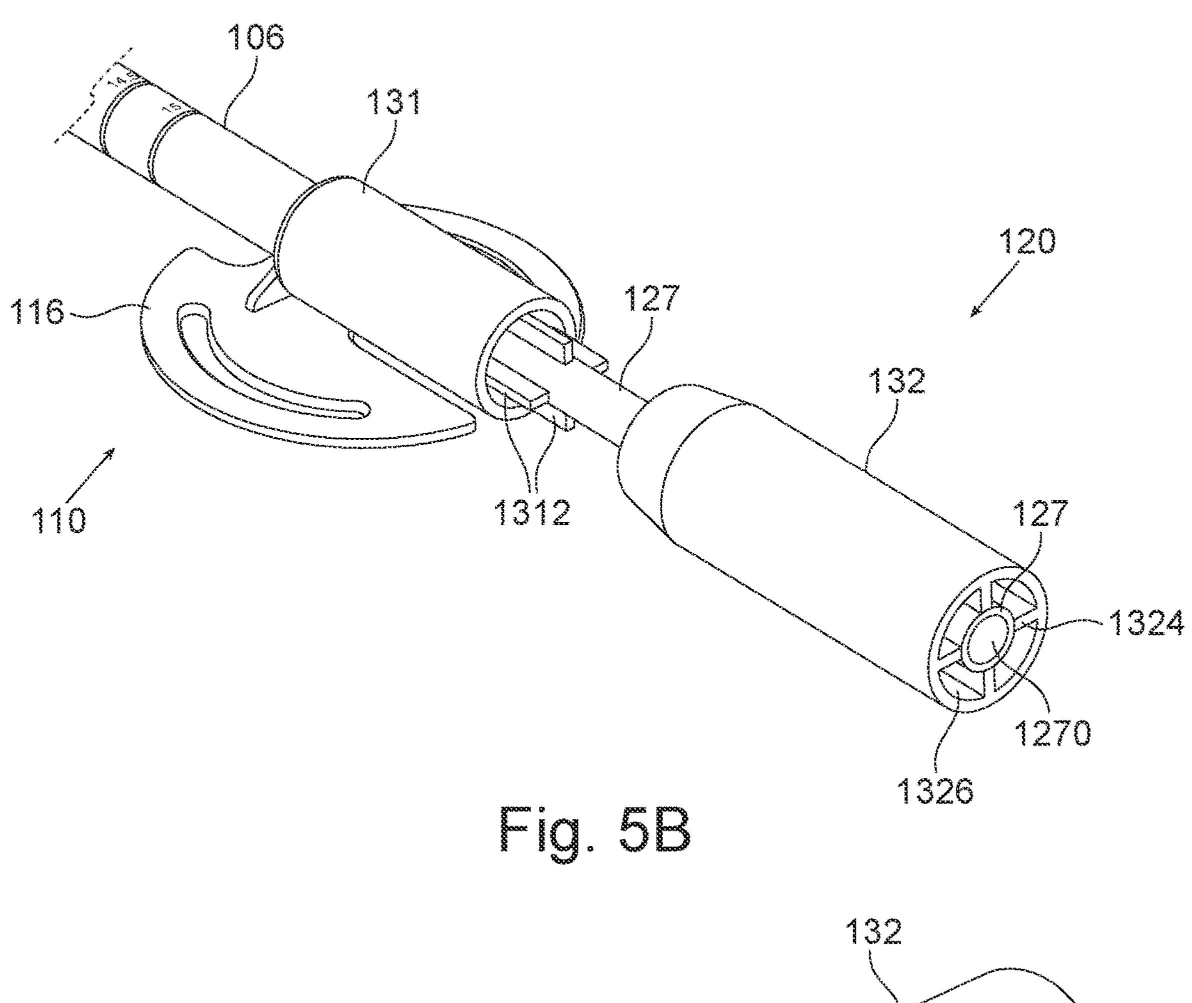
FIGS. 5B-5C are schematic back and front isometric partial view illustrations of the connection area between the inner lumen and the outer lumen of the dual lumen cannula of FIG. 2A according to some optional embodiments of the invention.
Figure 5C:
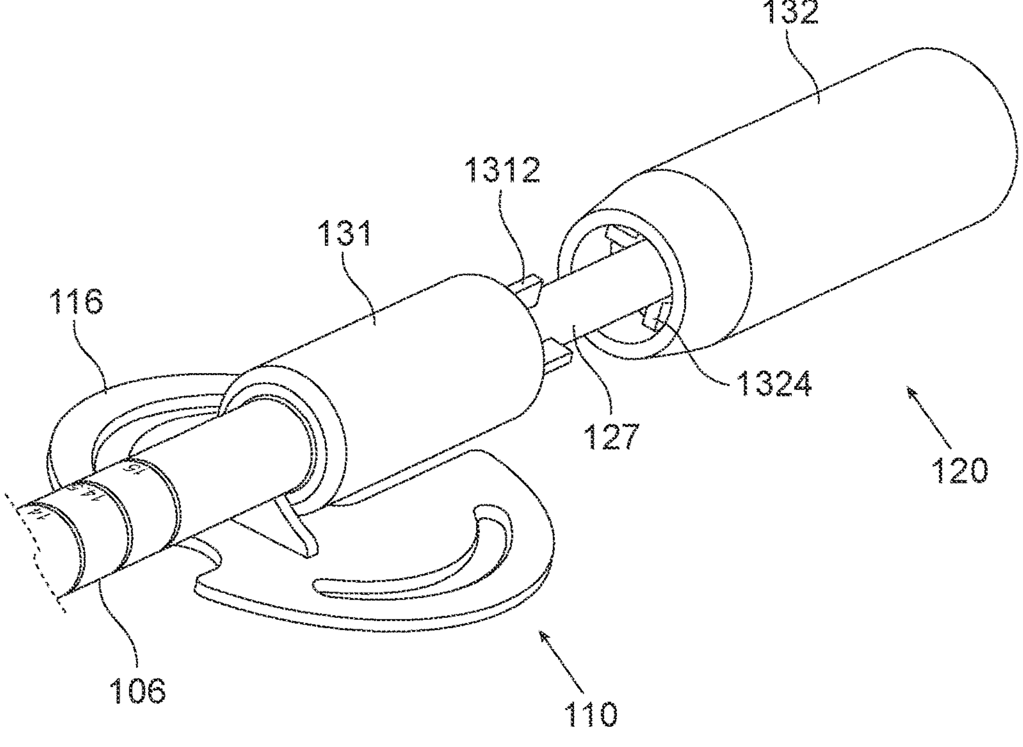

FIGS. 5B-5C are schematic back and front isometric partial view illustrations of the connection area between inner lumen 120 and outer lumen 110 of dual lumen cannula 200 of FIG. 2A according to some optional embodiments of the invention. In this view, cannula 127 is connected at its proximal end to inner lumen connector unit 132 and is being inserted through its distal end into the proximal end of outer connector unit 131 in a manner that protruding elements 1312 of outer connector unit 131 are embracing cannula 127 and functionally create a mechanical support to centralize the positioning of cannula 127 within outer cannula 106 at its proximal end in addition to the narrowing structure of cannula 106 at its distal end. Protruding elements 1312 are then being inserted into the inner space of inner lumen connector unit 132. In some optional embodiments of the invention, cannula 127 is extended into inner lumen connector unit 132 until it reaches its proximal end. In such scenario, cannula 127 is connected to the outer circumference of inner lumen connector unit 132 by at least one vertical separating wall (septum) 1324. In the specific example illustrated in this drawing inner lumen connector unit 132 contains four separating walls 1324 and the drained blood flows from the patient's vascular system through outer lumen 110 into chambers 1326 that are created between the separating walls 1324 and cannula 127, while the infused blood flows back unto the body via lumen (opening) 1270 of cannula 127. Also shown in these drawings butterfly with suturing holes 116 (also denoted "suturing element") that is used to fixate outer cannula 110 to the patient's skin with standard sutures, for safer usage of the dual lumen cannula 200 of this invention. As noted above, other fastening means such as rubber band, external fixation device, and the like, may be used additionally or alternatively. In some other optional embodiments of the invention, the inner cannula 127 is extended only until the distal end of inner lumen connector unit 132 and a central hollow tube-like structure within connector unit 132 functions as an extension of inner cannula 127 and replacing it.

Figure 6A:
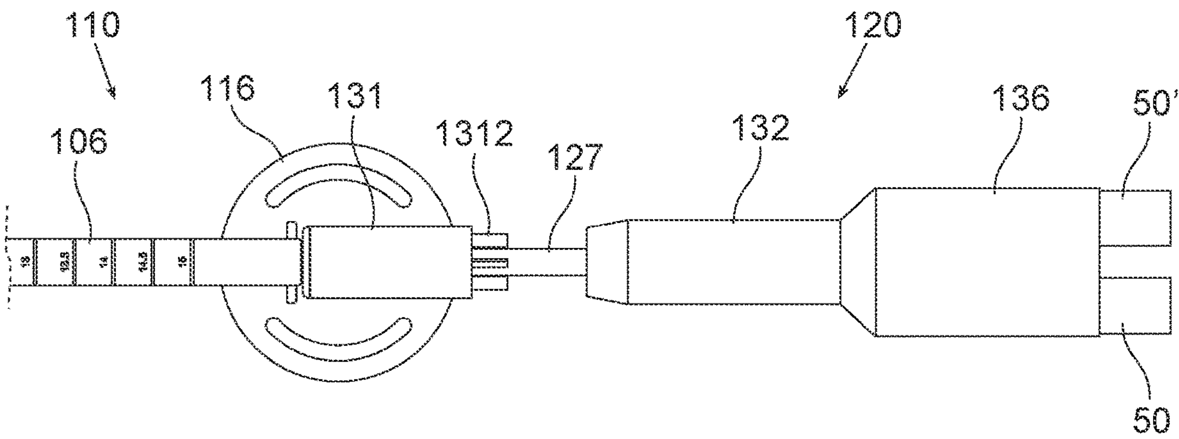
FIGS. 6A-6B are schematic top view and cross section partial views of the connection area between the inner lumen and the outer lumen of the dual lumen cannula of FIG. 2A including the flow router connector, according to some optional embodiments of the invention.
Figure 6B:
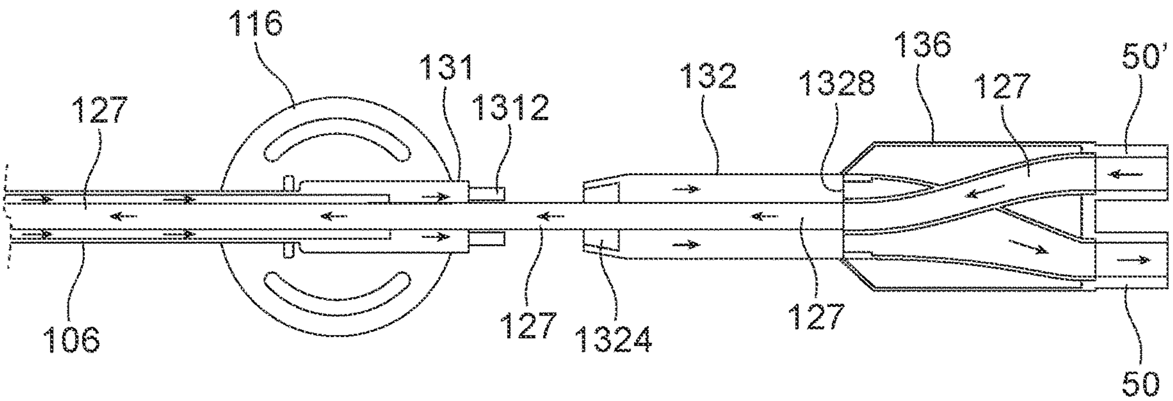

FIGS. 6A-6B are schematic top view and cross section partial views of the connection area of inner lumen cannula 120 and outer lumen cannula 110 of dual lumen cannula 200 of FIG. 2A. Outer connector unit 131 is attached to cannula 106 at its distal end and to suturing element 116 at the bottom side. Outer connector unit 131 having protruding elements 1312 at its proximal side ready to be inserted into a complementary space within inner lumen connector unit 132 and embracing cannula 127 of inner lumen cannula 120. Flow router connector 136 is also shown in these drawings, while it is being attached to inner lumen connector unit 132. As mentioned before, flow router 136 is to be considered as the third connector unit of the connector assembly of this invention and may be a separate unit or an integral unit of inner lumen connector unit 132. In a scenario that flow router 136 is a separated independent unit it may be assembled with inner lumen connector unit 132 by any suitable connecting means known in the art. For example, the operator may snap them one into the other, or lock them by Luer lock, or fasten one onto the other, for example by using fastening ring, and the like. The infused blood and the drained blood are transported from and machine to the patient's body and vice versa by tubes (not shown) connected to tube connector platforms 50 and 50' that extend from flow router 136 toward the extracorporeal machine.

In the cross section partial view, the opposite flow directions of the drained blood and the infused blood within inner infusion cannula 120 and outer drainage cannula 110 is illustrated. For simplicity of explanation, connector unit 131 of outer lumen cannula and connector unit 132 of inner lumen cannula are separated to clearly demonstrate the parts related to the connection. The blood flow begins only when the two cannulas are coupled. Also shown in this cross section, cannula 106 embracing cannula 127. The blood flow in both lumens as well as in connector units 131 and 132 is performed in parallel lumens and opposite directions as indicated by the arrows along the cannulas. Flow router 136 gathers all the drained blood that flows in chambers 1326 together into one tube that will be connected to tube connector platform 50 to transport the blood into the extracorporeal machine for treatment. In the same manner but in the opposite direction, treated blood from the extracorporeal machine is infused back into the vascular system of the treated patients through a tube that will be connected to tube connector platform 50' to transports the treated blood through flow router 136 into cannula 127 toward the patient's body.

Figure 6C:
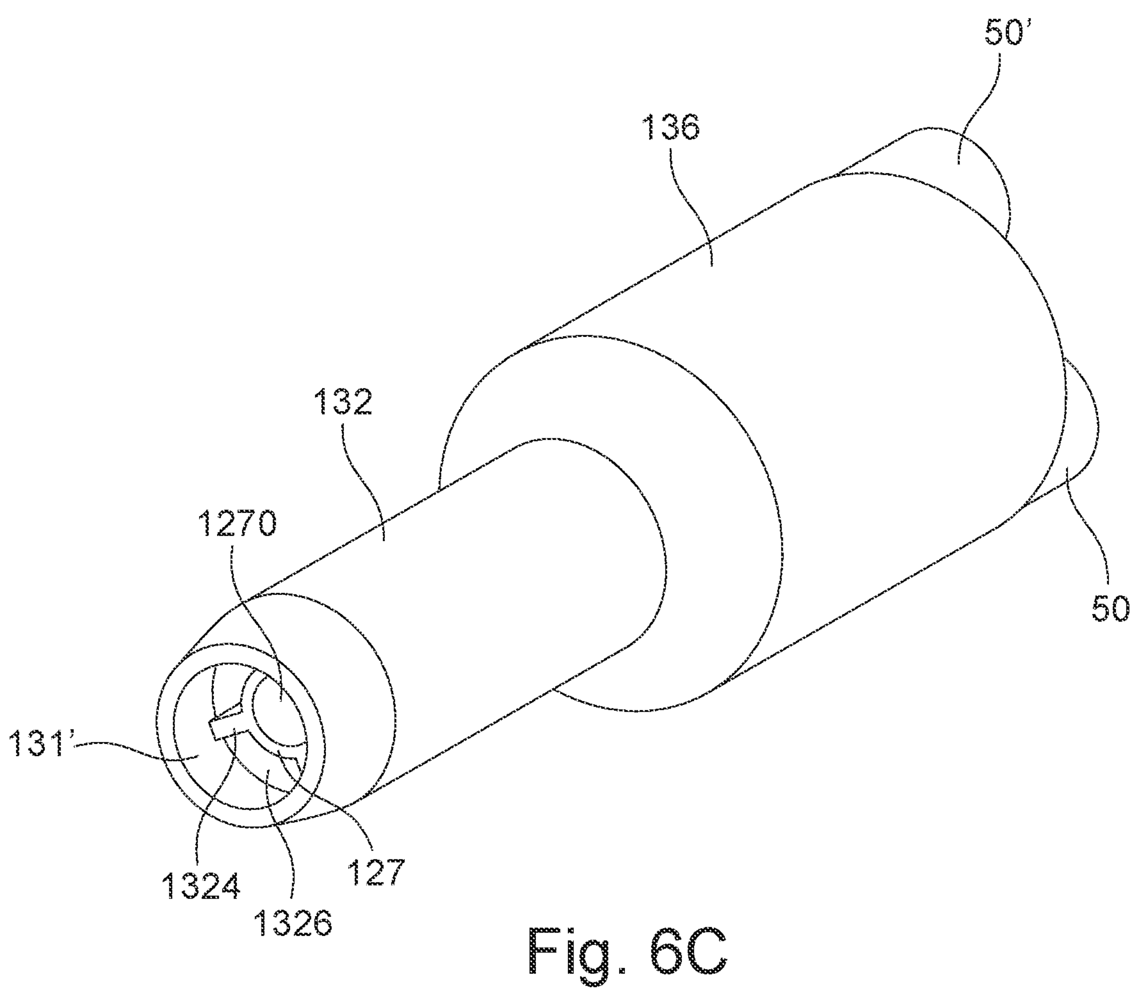
FIGS. 6C-6D are schematic isometric view and cross section view, respectively, of the connector unit of inner lumen cannula and the flow router of the dual lumen cannula of FIG. 2A according to some optional embodiments of the invention.
Figure 6D:
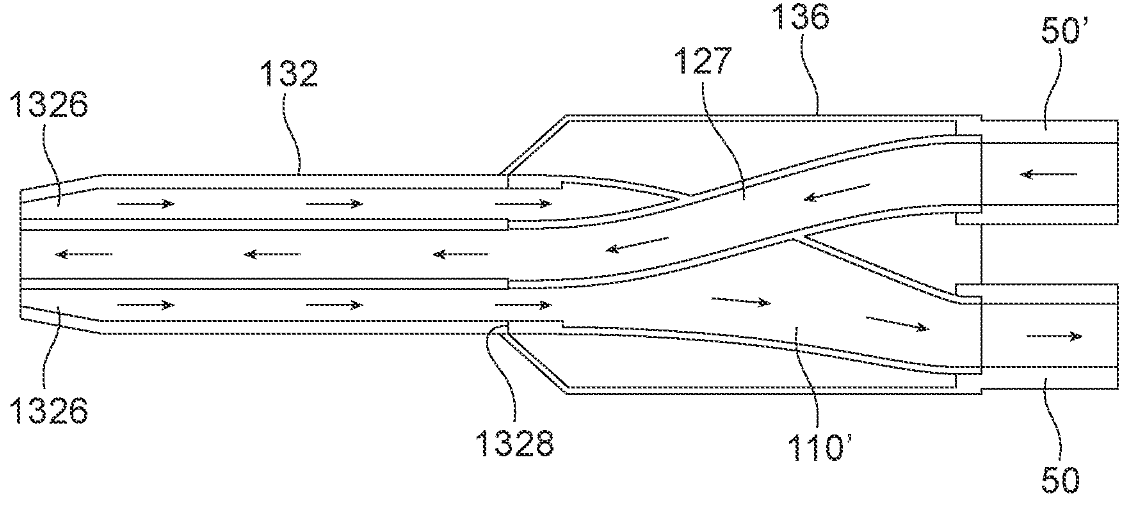

FIGS. 6C-6D are schematic isometric view and cross section view, respectively, of inner lumen connector unit 132 and flow router 136 of dual lumen cannula 200 of FIG. 2A according to some optional embodiments of the invention. Flow router 136 gathers the drained blood from outer tube 110 through the different chambers 1326 of inner lumen connector unit 132 into a single tube connected to tube connector platform 50 transporting the drained blood into the extracorporeal machine. Flow router 136 also routes the blood flowing from the extracorporeal machine through a tube connected to tube connector platform 50' in a manner that blood that flows in two separate adjacent tubes is converted to flow in two lumens inserted one within the other, while the opposite flow direction is maintained.

At the isometric view (FIG. 6C) inner lumen connector unit 132 and flow router 136 are connected to each other and tubes connector platforms 50 and 50' are partially shown at the proximal end of flow router 136. The isometric view further illustrates cannula 127 and lumen 1270 shown at the distal end of inner lumen connector unit 132, separating walls 1324, chambers 1326, and area 131' to which outer connector unit 131 with protruding elements 1312 are connected thereto. The cross-section view (FIG. 6C) shows the treated blood flow within cannula 127 from tube connected to tube connector platform 50' toward the patient's vascular system. At the opposite direction, the drained blood that flows out from the body through outer lumen 110 is entering chambers 1326 of inner lumen connector unit 132 that functionally serve as the extension of outer lumen 110 to transport the drained blood out from the body to the extracorporeal machine via a tube configured to be connected to tube connector platform 50. The blood from chambers 1326 is preferably gathered within flow router 136 into a single chamber 110' that is connected at its proximal end to tube connector platform 50 that transport the drained blood into a tube connected to the extracorporeal machine.

The extracorporeal machines that may be implemented with the dual lumen cannulas 100 and 200 of the invention are preferably extracorporeal oxygenation systems and dialysis systems.

Figure 6E:
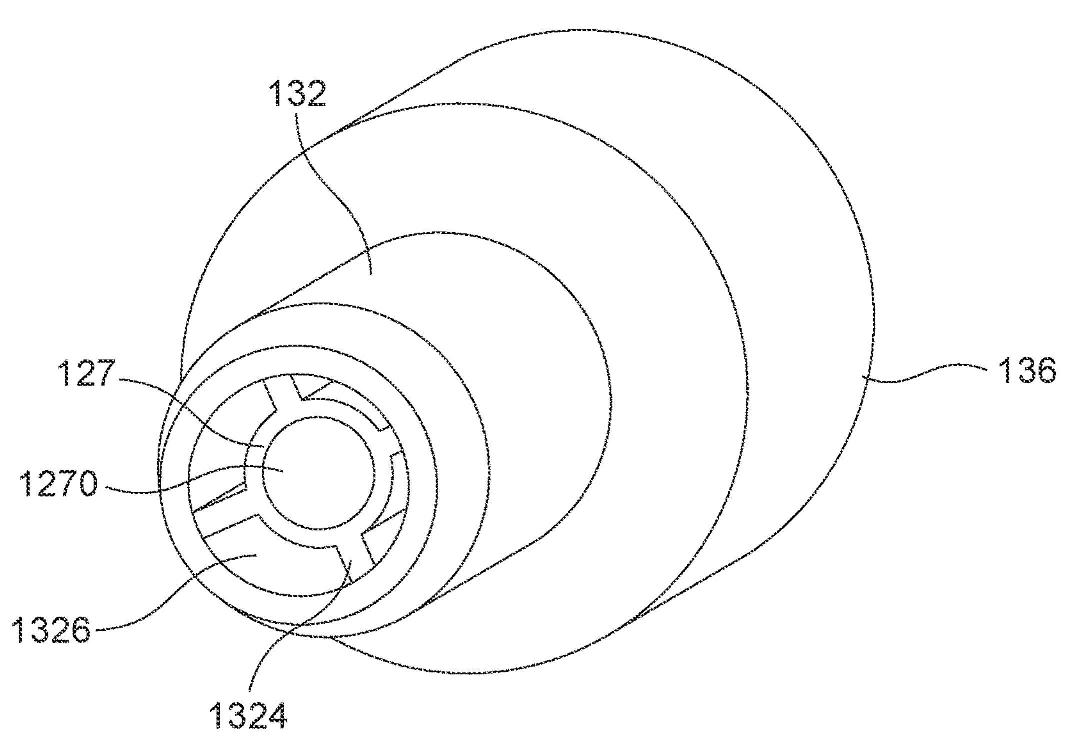
FIGS. 6E-6F are schematic isometric front view and isometric back view respectively, of the connector unit of inner lumen cannula and the flow router of the dual lumen cannula of FIG. 2A according to some optional embodiments of the invention.
Figure 6F:
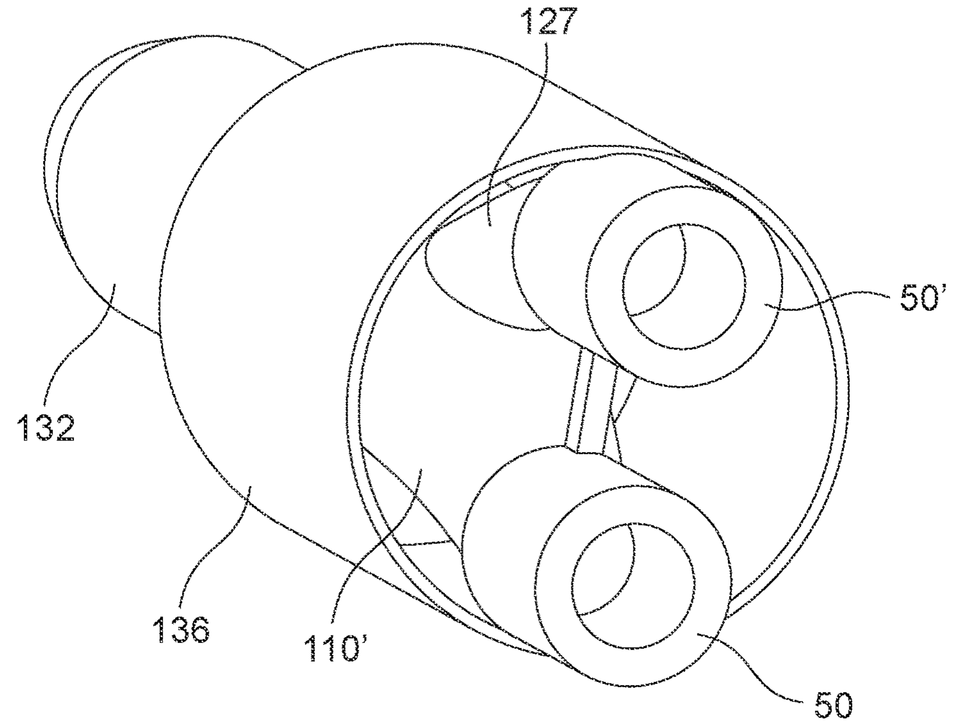

FIGS. 6E-6F are schematic isometric front view and isometric back view respectively, of the inner lumen connector unit 132 of inner lumen cannula 120 and flow router 136 of dual lumen cannula 200 of FIG. 2A according to some optional embodiments of the invention. In the isometric front view (FIG. 6E) four chambers 1326 created at the interface of separating walls 1324 and cannula 127 are clearly shown. Blood drained from the patient's body is transported to the extracorporeal machine via these chambers, while the returning blood that is about to be infused back into the vascular system of the patient flows within lumen 1270 of cannula 127 until it reached infusion openings 122 and infused back to the body. The isometric back view (FIG. 6F) demonstrates the connection of flow router 136 to tube connecter platforms 50 and 50' that transport the drained blood from the body through drainage openings 112 of outer lumen through cannula 106 into chambers 1326 of inner lumen connector unit 132 that are all collected into a single chamber 110' of flow router 136 and transported to a tube (not shown) connected to tube connector platform 50 into the extracorporeal machine. Also shown at the back view, the entrance point of the treated blood from the extracorporeal machine through a tube (not shown) connected to tube connector platform 50' and then into cannula 127 that extends from the proximal end of flow router 136 through inner lumen connector unit 132, and further through outer connector unit 131 into cannula 106 until it extends out of its distal end up to the target area. In fact, cannula 127 in this optional implementation of the invention passes through the entire connector assembly 130, through cannula 106 until it reaches the target area and infuses blood through infusion openings 122. However, in some optional embodiments, inner cannula 127 may extend up to the distal end of connector unit 132 and from that point up to the tube connected to tube connector platform 50' the treated blood flows through dedicated chambers within flow router 136 and connector unit 132 until they reach inner cannula 127.

Figure 6G:
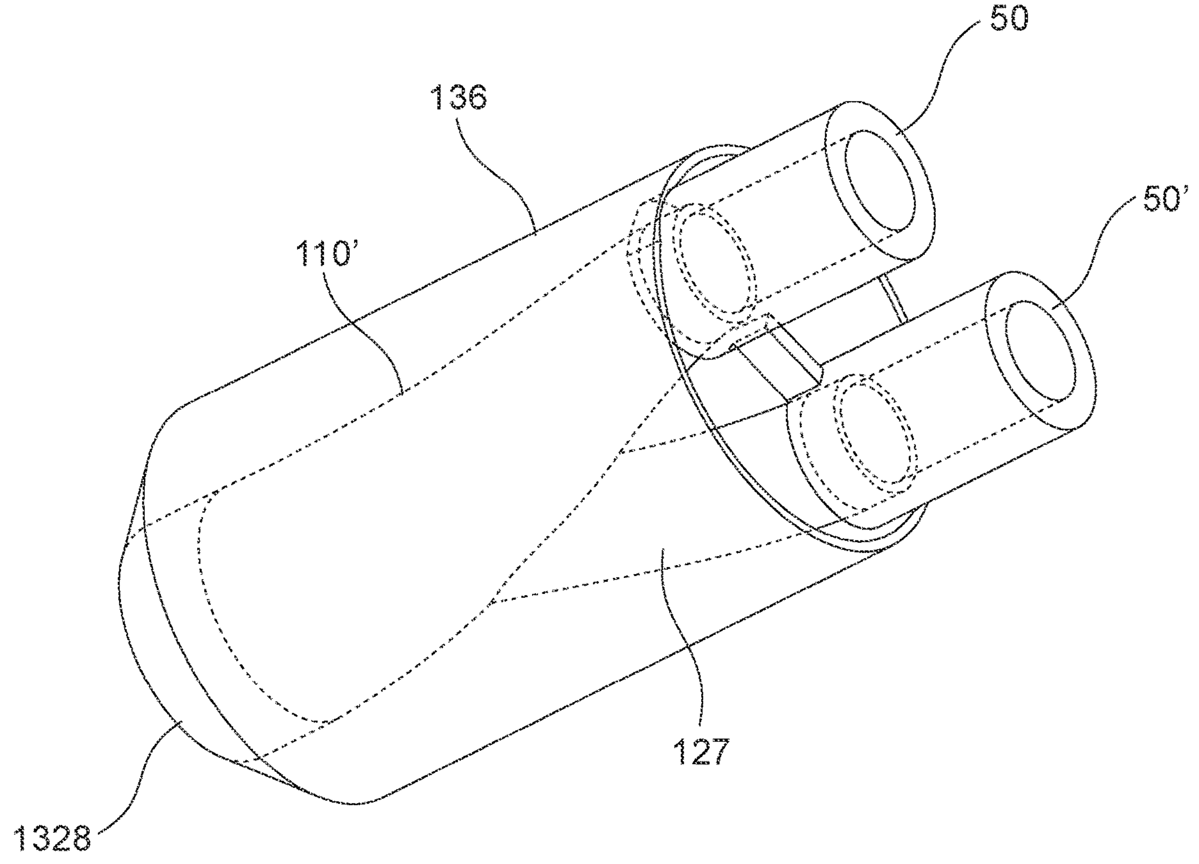
FIG. 6G is a schematic isometric side view of the flow router of FIG. 2A in a position simulating the position of the unit while the dual lumen cannula of the invention is in use with the housing of the flow router transparent showing the inner components according to some optional embodiments of the invention.

FIG. 6G is a schematic isometric side view of flow router 136 of FIG. 2A in a position simulating the position of the unit while the dual lumen cannula is in use and connected to the patient's body, with the housing of flow router 136 transparent showing the inner components according to some optional embodiments of the invention. In this view, tube connector platforms 50 and 50' are positioned upward. As previously described tube connector platform 50' in one optional embodiment is connected to cannula 127 at one end and to a tube (not shown) that transport blood from the extracorporeal machine into the patient's body, while tube connector platform 50 is connected to chamber 110' at one end and to a tube (not shown) at the other end for transporting blood suctioned from the body into the extracorporeal machine. Also shown in this position connection area 1328 of flow router 136 and inner lumen connector unit 132, and the inner components of flow router 136 including cannula 127 and chamber 110'.

In a typical implementation of the dual lumen cannulas 100 and 200 provided herein, the inner lumen is an infusion lumen, for delivering treated blood back into the patient's vascular system, and the outer lumen is a drainage lumen, for removing untreated blood from the vascular system. However, in some other optional implementations of the invention, the outer lumen may be used to return the blood into the body, while the inner lumen is used to drain blood from the body. In addition, inner lumen 120 has a longer extension than outer lumen 110. An advantage of inner lumen being longer than the outer lumen, and inner lumen being the infusion lumen, is that the treated blood is deposited into the vascular system downstream of the drainage lumen. This orientation reduces the likelihood of cyclic flow of treated blood from the infusion lumen 120 to the drainage lumen 110 and back into the blood treatment system.

In exemplary, none limiting examples, inner lumen 120 is sized of sufficient length and diameter to be inserted into the femoral veins and/or to the superior vena cava via a major vein superior to the heart. The major veins are included, but not limited to, the right and left internal jugular veins, the right and left external jugular veins, and the right and left brachiocephalic veins. The dimensions of the inner lumen and the outer lumen may be dictated by considerations such as the size of the patient and the desired volume and flow rate of the blood through the lumens. In exemplary embodiments, inner lumen 120 has a length of between 10 and 40 mm and a diameter of between 5 and 16 Fr, and outer lumen 110 has a length of between 10 and 40 mm and a diameter of between 10 and 24 Fr.

The connection between inner lumen and outer lumen may be reversible and they can be separated thereof. Upon insertion of the inner lumen into the outer lumen, the position of one lumen related to the other is fixed and predetermined by the connector units connected to each one of the cannulas respectively.

Connector assembly 130 is depicted schematically and it should be clear to man in the art that the connector assembly and each one of its units and the connection therebetween may take any other form suitable for converting an inner and outer tube into side by side tubing, as long as its functionality remains the same.

Drainage lumen 110 includes openings 112 for sucking blood therethrough from the patient vascular system. Openings 112 are suction holes, and blood is drawn therethrough by the force of a pump that is part of the extracorporeal blood treatment machine. Openings 112 are preferably located at the distal end of drainage lumen 110. In some embodiment, openings 112 are sized and situated on the side of the distal end of drainage lumen 110 in order to prevent blocking of blood draining during suction. Blocking may occur due to clotting or vein adhesion to the drainage lumen due to suction forces.

Introducing the dual lumen cannula 100, 200 of this invention into the patient's vascular system proceeds as follows. First, outer lumen 110 is inserted into the patient's vascular system. The outer lumen may be sutured to the skin of the patient by stitching regular sutures through butterfly 116. Typically, the outer lumen is inserted through use of an introducer, and optionally a guide wire, drawn through the outer lumen 110 up to its distal end according to common practice (Seldinger technique). As a result, there is no need to prime the outer lumen cannula prior to insertion since the presence of the introducer prevents formation of air bubbles. When the introducer and guidewire are withdrawn, the withdrawal causes a small vacuum to form in the outer lumen 110, which is back filled with blood.

Next, the inner infusion lumen 120 is preferably pre-primed through use of a priming cap (not shown) that may be connected to a priming system. The priming system may be a standalone system or may be integrated with the blood extracorporeal machine. Following completion of the priming, the priming cap is removed.

Next inner lumen 120 is inserted into the outer lumen 110 through the outer lumen connector unit (either 108 or 131). The inner lumen 120 is advanced to protrude through outer lumen 110, until the connectors of each lumen are coupled. Inner lumen 120 is fixed to the outer lumen 110 when the connector assembly units are connected. Once the two lumens are connected, they function as a single dual lumen cannula 100, 200.

The insertion of the inner lumen is performed with minimal strain on the patient. In addition, because the inner lumen 120 is already fully primed prior to connection, there is no need to prime open connection ports during the connection process, as in other dual lumen cannulas known in the art. Accordingly, the cannulation process for the dual lumen cannula of this invention is significantly easier, and safer, than cannulation of other dual lumen cannulas available in the market.

In particular, the described method is especially advantageous compared to an alternative dual lumen cannula system, in which the two lumens are inserted as single units separated thereof and are advanced to the desired location in the body while connected to each other, before the inner lumen is further advanced relative to the outer lumen. Moving both the inner and outer lumens simultaneously may cause application of greater force on the blood vessels, and correspondingly requires greater technical skill to perform without injuring the patient. By contrast, when the outer lumen 110 is sutured into place before insertion of the inner lumen 120, it is only necessary to advance the inner lumen 120 relative to the outer lumen 110. In addition, inserting the inner lumen separate from the outer lumen allows for pre-priming the inner lumen prior to connection. After placement of the inner lumen cannula within the outer lumen cannula, fluid tight connections may be formed.

In some optional embodiments, the inner diameter of outer cannula 106 at the distal end is sized to be only slightly wider than the outer diameter of inner cannula 127. This sizing enables free sliding of the inner cannula 127 through narrow area 111, while also minimizing inefficiencies resulting from the flow of blood through the area 111 instead of continuing through outer cannula 127.

In the described embodiments, the proximal point of connection between inner lumen 120 and outer lumen 110 is fixed. Thus, inner lumen 120 always extends a specified distance beyond outer lumen 110.

Preferably, the dual lumen cannulas are designed such that, after treated blood enters the body via the infusion lumen, the blood circulates throughout the entire bloodstream before being removed via the drainage lumen.

In one main aspect, the present invention is aimed to provide a convenient and safe solution that allows practitioners to insert a dual lumen cannula as simple and safe as inserting a single lumen cannula and transform it to a single lumen cannula upon need to increase the oxygenation flow rate and vice versa, in a simple and convenient manner. Beside the simplicity of inserting the cannula into the target area and advantage to the medical team, the novel solution is also beneficial to the patient as it allows to thread the second lumen through the first lumen in vivo, one into the other, after insertion of the first single lumen, and to detach the inner lumen upon need and transform the dual lumen cannula back into a single lumen cannula in a safe, fast and easy manner. And then, insert second lumen in another blood vessel according to common practice.

Figures 7A, 7B:
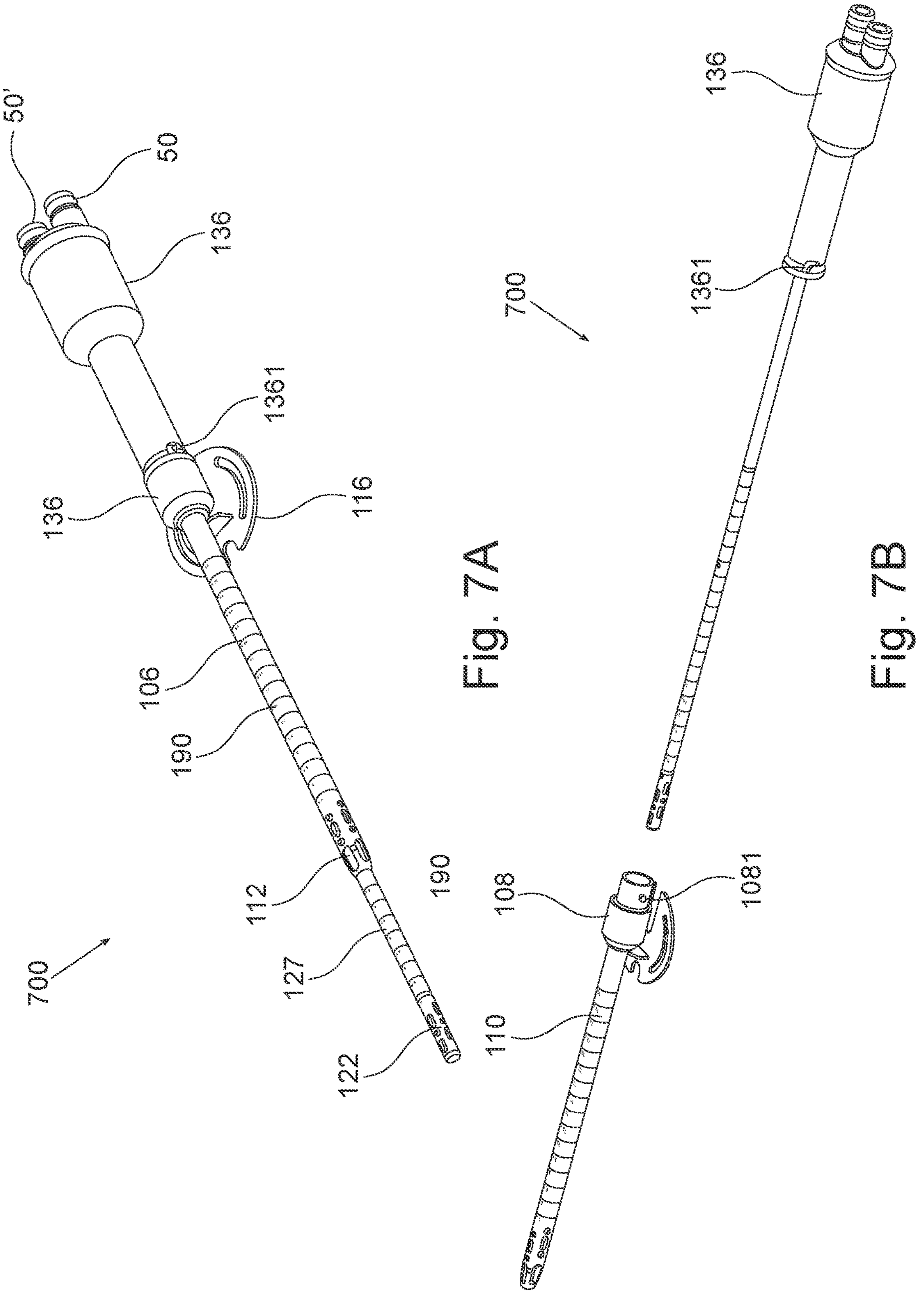
FIG. 7A is an isometric view of at least one embodiment of the inventive dual lumen cannula in an assembled, ready to use form comprising a drainage outer lumen and an infusion inner lumen connected therethrough by a connector assembly according to optional embodiments of the invention.
FIG. 7B is a schematic exploded view illustration of the dual lumen cannula of FIG. 7A illustrating major components of the dual lumen cannula of the invention in a dual lumen configuration.

FIG. 7A is a schematic isometric view illustration of a transformable dual lumen cannula 700 of the invention in an assembled, ready to use form. In this form, the dual lumen cannula 700 comprises a drainage outer lumen 110 configured to drain blood through drainage openings 112 of cannula 106 from the body of a treated patient toward an extracorporeal machine for treating the drained blood, and an infusion inner lumen 120 configured to infuse blood through infusion opening 122 of cannula 127 from the extracorporeal machine back into the body of the treated patient, the inner and outer lumens are connected to each other by a connector assembly that connect the two lumens and route the blood flow in each of them as will be described in details below. Cannula 106 of the outer lumen may comprise calibration marks 190 to thereby provide the medical team indication about the penetration length. In a similar manner, cannula 127 of the inner lumen may also contain calibration marks 190 to monitor the penetration length of the inner lumen.

The inner lumen comprises a connector unit 108 that is preferably but not necessarily, an integral part of the inner lumen. Optionally, connector unit 108 is connected to a butterfly with suturing holes 116 that may be fixed to a patient's skin with standard sutures, to stabilize the position of the dual lumen cannula during the medical treatment. It should be clear that other means to stabilize and fasten the cannula to the patient's body may be used and butterfly 116 is only one none-limiting exemplary implementation. Connector unit 108 of the inner lumen is functionally connected at its proximal end to a connector unit 136 also referred hereinafter as "flow router" 136. Flow router 136 is the connecting unit between the dual lumen cannula and the extracorporeal machine, and it is configured and operable to set the blood flow in opposite directions between the inner and outer lumens and preferable from a flow at two separated parallel tubes into a flow within two insertable one into the other lumens. In the specific example illustrated herein, connector unit 108 is designed at its proximal end as a bayonet connector having a complimentary shape 1081 (shown in FIGS. 7B-7C) suitable to be mounted on the distal end of flow router 136 onto complementary area 1361 to allow simple and slight attachment and detachment of the connectors. It should be clear that usage of bayonet connector is only one optional embodiment that can be implemented for connecting the inner lumen to the outer lumen to thereby assemble the transformable dual lumen cannula of the invention and other connectors with different solutions may also be implied.

The connection between the inner lumen and the outer lumen is performed in vivo, within the patient's body, as the outer lumen is first inserted into the patient as a single lumen cannula and only afterward, the inner lumen is threaded into the outer lumen until they are coupled into a dual lumen cannula. Also shown in this drawing tube connection platform 50 and 50' that are connected to flow router 136 and allow the connection of the dual lumen cannula of the invention to tubes for transporting blood from the patient's body toward the extracorporeal machine and for transporting oxygenated blood on the opposite direction, from the extracorporeal machine towards the patient's body. Also shown in this view, a butterfly like structure with suture holes 116 connected to outer lumen 110, which is used for stitching the dual lumen cannula of the invention to the patient's skin during the medical process to secure it.

FIG. 7B is a schematic exploded view illustration of the transformable dual lumen cannula 700 of FIG. 1A in a dual lumen form, illustrating the major components of the device. At this form, transformable dual lumen cannula 100 is composed of the outer lumen 110 comprising connector 108 and inner lumen 120 comprising connector 136 that also functions as a flow router 136 that comprise at its proximal end tube connection platforms 50 and 50' to thereby allow transport of the blood into and from the medical machine. In some optional embodiments of the invention, flow router 136 is an independent, separated part connected to the proximal end of inner lumen 120 or an integral part thereof. As shown in this view, the inner lumen is designed to be threaded through outer lumen 110 that is inserted to the patient's blood vessel as a single lumen.

Figures 7C, 7D:
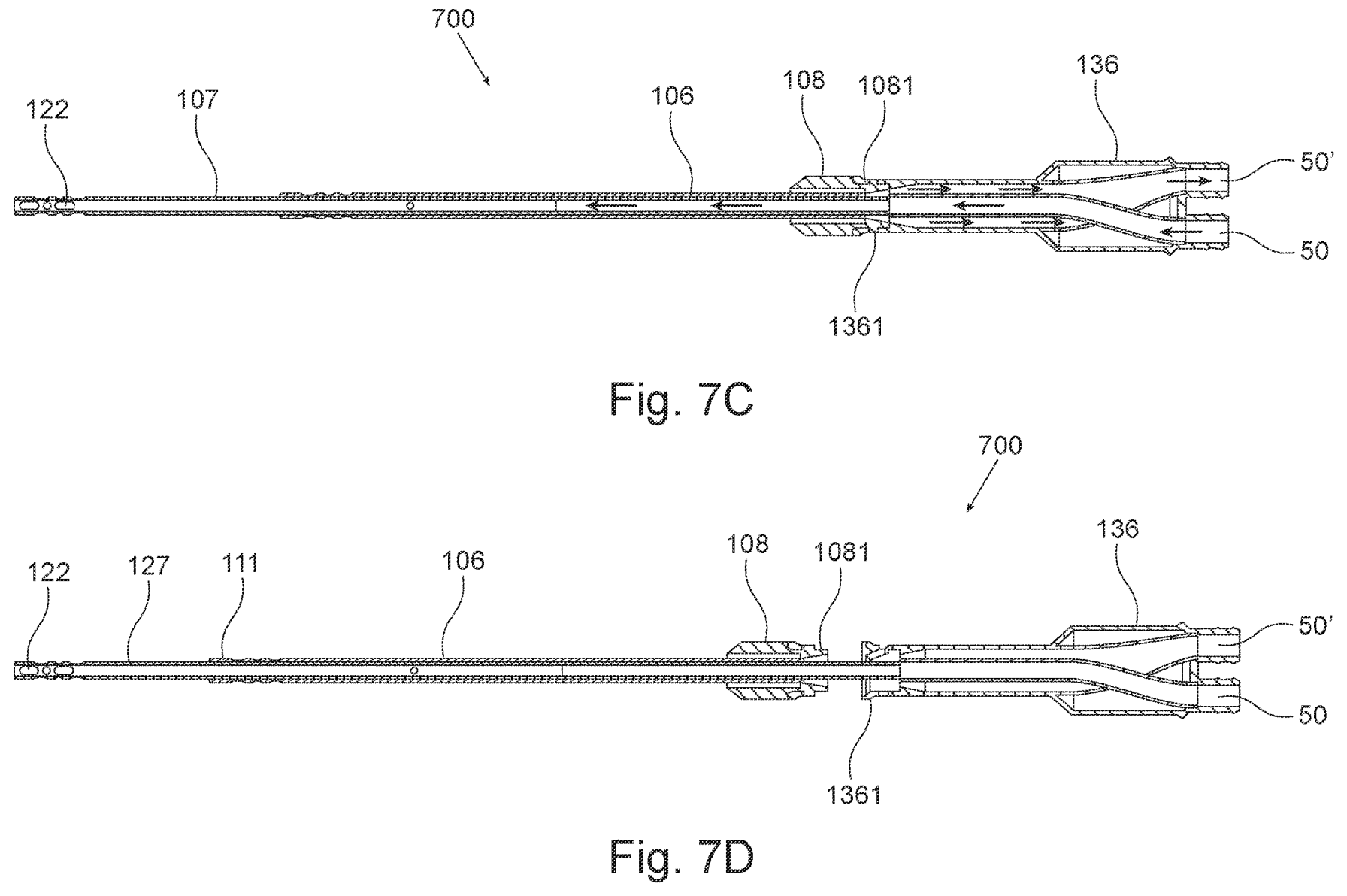

FIGS. 7C-7D are schematic cross section views of the transformable dual lumen cannula 700 of FIG. 7A, wherein, FIG. 7C illustrates the cannula in an assembled form when the inner lumen and the outer lumen are connected therethrough, and FIG. 7D illustrated the transformable dual lumen cannula in a partially assembled form, in which the infusion inner lumen is inserted into the drainage outer however, connector units 108 and 136 are detached from each other, either before connection, so as to transform the single lumen cannula into a dual lumen cannula, or after connection, so as to transform the dual lumen cannula into a single lumen cannula as needed. As previously described in PCT/IL2021/051335, outer lumen 110 comprises at least a cannula 106, also denoted interchangeably "inner cannula" and "infusion cannula", having a diameter that is larger than the diameter of the inner lumen 120 to allow the insertion of inner lumen 120 through it. Cannula 106 has a narrow area 111 at its distal end mainly for centralizing the position of the inner lumen toward the target area, and at least one drainage opening 112. Optionally, cannula 106 contains calibration marks on it that may further be marked with numbers to indicate the penetration length of outer lumen 110 into the patient's body.

Figures 8A, 8B:
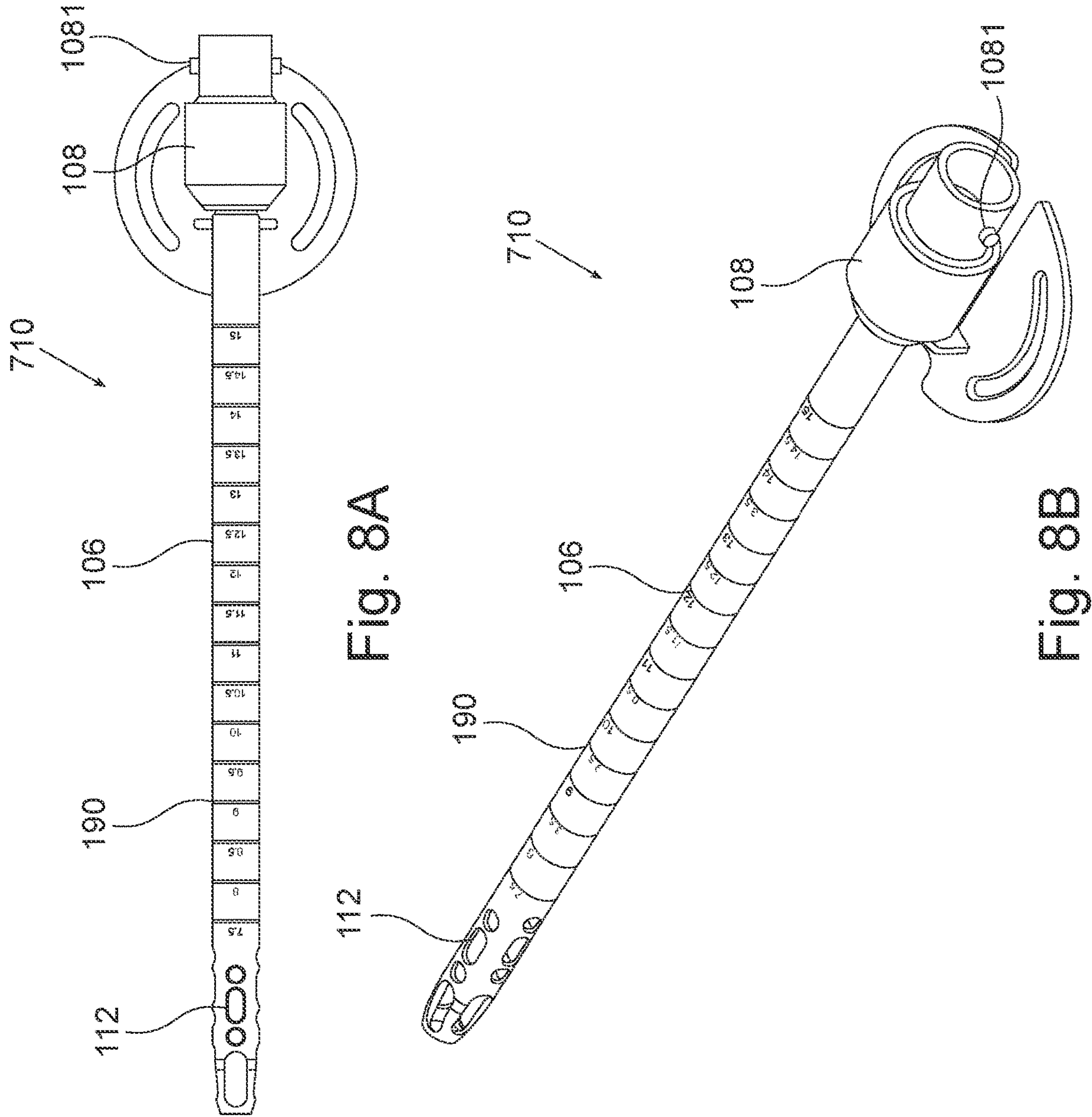
FIGS. 8A-8B are schematic top view and isometric back view illustrations respectively of the drainage outer lumen of dual lumen cannula of FIG. 7A in accordance with some optional embodiments of the invention.

FIGS. 8A-8B are schematic top view and isometric back view illustrations respectively of the drainage outer lumen 110 of the transformable dual lumen cannula 700 of FIG. 7A in accordance with some optional embodiments of the invention. Shown in these views: cannula 106, connector unit 108 having at its proximal end bayonet connector 1081 for simple and fast connection in vivo to a matching connector, according to its use as a single lumen cannula or as a dual lumen cannula. When drainage lumen 110 is used as a dual lumen cannula, connector unit 108 is assembled with infusion inner lumen 120 via connector 136. However, when drainage lumen 110 is transformed to function as a single lumen cannula, connector unit 108 is assembled with a suitable connector as will be described in detail with reference to FIGS. 10A-10C hereinbelow. Also shown in these drawings are butterfly like structure with suture holes 116, calibration marks 190 and drainage openings 112.

Figures 9A, 9B:
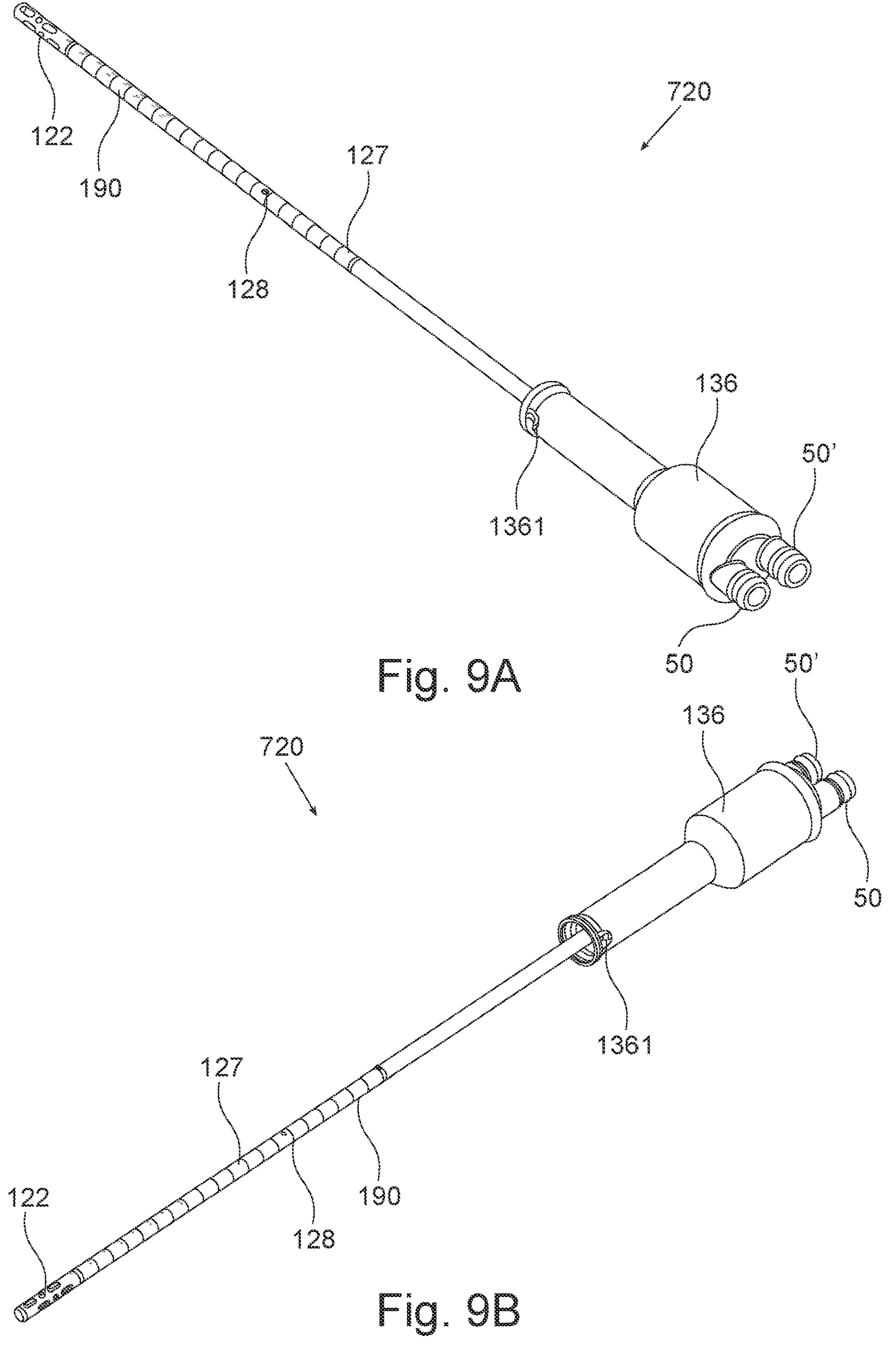
FIGS. 9A-9B are schematic isometric top back view and isometric top front views respectively of at least one embodiment of infusion inner lumen of the transformable dual lumen cannula of FIG. 7A in accordance with some optional embodiments of the invention.

FIGS. 9A-9B are schematic isometric top back view and isometric top front views respectively of at least one embodiment of infusion inner lumen 120 of the transformable dual lumen cannula of FIG. 7A in accordance with some optional embodiments of the invention. Infusion inner lumen 120 of transformable dual lumen cannula 700 comprises at least the following: cannula 127 has a smaller diameter relative to cannula 106 that allows its insertion through cannula 106 and a longer length that allow it to extend beyond cannula 106 to a target area. Cannula 127 comprises at least one infusion opening 122 at its distal end that allow to return treated blood (mostly, oxygenated blood) from the extracorporeal machine back to the patient's vascular system. Cannula 127 may further comprise a pressure regulation hole 128 that is formed along the perimeter of the inner lumen as may be used to alleviate high pressure situations in the infusion lumen, which may lead to cavitation as described in detail in PCT/IL2021/051335.

Inner lumen 120 comprises infusion openings 122 for fluidic connection to the patient's vascular system. These openings form a gateway for treated blood to flow back into the cardiovascular system. Also shown in these drawings, calibration marks 190 and tubes 50 and 50' that transport the blood into and from the medical machine.

Figures 10A, 10B, 10C:
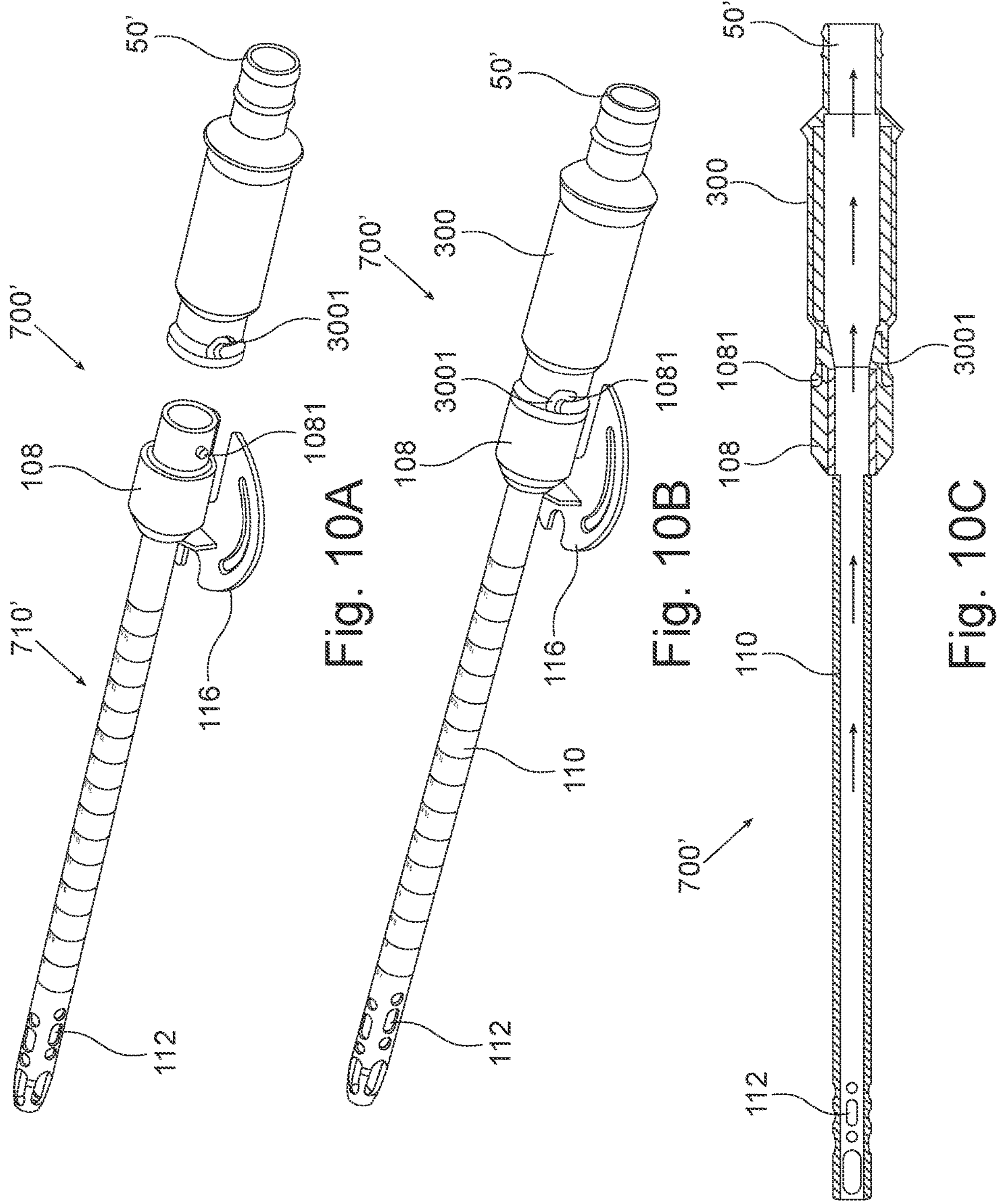

FIG. 10A illustrates drainage outer lumen 110 ready to be connected to a single lumen connector 300 that allows the connection of lumen 110 to the extracorporeal oxygenation system to allow drainage of blood from the patient to the machine. It should be clear that in some optional embodiments the outer lumen may be the infusion lumen that infuses oxygenated blood from the machine to the patient's body. In the specific example illustrated herein, when the medical condition of the patient changes and dual lumen cannula is not suitable any longer since high flow approach should be used, the physician simply detaches the inner cannula from the outer cannula, for example by rotating bayonet connectors 1081 and 1361 until they are separable. Upon detachment of the inner and outer lumens one from the other, the inner lumen is removed from the patient's body, and is being replaced by a single lumen connector 300 that is now assembled onto the proximal end of drainage lumen 110 to allow its connection to the extracorporeal oxygenation system, or to any other system in use. Infusion of treated blood is conducted through additional single lumen cannula being inserted to the patient's body in accordance with common practice.

FIGS. 10B and 10C illustrate the drainage outer lumen 110 while being connected to the single lumen connector 300 ready to be used as a single lumen cannula having a single blood flow direction in an isometric view and cross section view respectively, in accordance with optional embodiments of the invention. These drawings illustrate the complementary structure of connector 108 and connector 300 that functionally replaces connector 136 of the dual lumen cannula to thereby allow the connection of the outer lumen 110 through tube connector platform 50' to the device in use and drainage or infusion of blood in high flow rate.

It should be clear that the description of the embodiments and attached Figures set forth in this specification serves only for a better understanding of the invention, without limiting its scope. It should also be clear that a person skilled in the art, after reading the present specification could make adjustments or amendments to the attached Figures and above-described embodiments that would still be covered by the present invention.

The invention claimed is:

1. A cannula configured to transform between a dual lumen cannula into a single lumen cannula, or configured to transform between the single lumen cannula into the dual lumen cannula, in a patient's vascular system in real time, in vivo, the cannula comprising:

at least one inner lumen having at least two ends, an inner lumen proximal end and an inner lumen distal end, a hollow intermediate extent between said at least two ends having one or more openings at the inner lumen distal end, and at least one inner lumen connector unit and at least one flow router at the inner lumen proximal end, wherein said at least one inner lumen is configured to be inserted into an at least one outer lumen;

said at least one outer lumen having at least two outer ends, an outer lumen proximal end and an outer lumen distal end, a hollow outer intermediate extent between said at least two outer ends having one or more openings, said hollow outer intermediate extent further comprising one or more openings at the outer lumen distal end, and at least one outer lumen connector unit at the outer lumen proximal end, wherein said outer lumen is configured to receive the at least one inner lumen;

at least one single flow connector adapted to be connected to said at least one outer lumen connector unit at the outer lumen proximal end having a single channel flow pattern; and at least one dual flow connector adapted to be connected to said at least one inner lumen connector unit at the inner lumen proximal end having a dual channel flow pattern;

wherein upon use as the single lumen cannula, said at least one outer lumen is configured to be in coupling contact with said at least one single flow connector when said at least one outer lumen has been installed in a patient;

wherein upon use as the dual lumen cannula, said at least one inner lumen is configured to be inserted into said at least one outer lumen in vivo until said inner lumen proximal end of said at least one inner lumen connector unit is in coupling contact with said at least one outer lumen connector unit, and a proximal end of said at least one inner lumen connector unit is configured to be in coupling contact with said at least one dual flow connector after said at least one outer lumen has been installed in the patient.

2. The cannula of claim 1, wherein said hollow intermediate extent of the at least one inner lumen further comprises one or more holes located between the outer lumen distal end and a proximal end of the at least one outer lumen, and within a region of the at least one inner lumen which is within the at least one outer lumen when assembled.

3. The cannula of claim 1, wherein said at least one outer lumen further comprises a narrow area at its distal end for centralizing the position of the at least one inner lumen toward a target area.

4. The cannula of claim 1, wherein said one or more openings on the hollow outer intermediate extent of the at least one outer lumen are at least one drainage opening.

5. The cannula of claim 1, wherein upon connection of said at least one outer lumen connector unit to said at least one inner lumen connector unit, the at least one inner lumen connector unit provides a flow path from the at least one flow router to both said at least one outer lumen and said at least one inner lumen.

6. The cannula of claim 1, wherein said at least one flow router further comprises an inlet port for connecting to one or more connector tubing connected to at least one medical device.

7. The cannula of claim 1, wherein said at least one outer lumen further comprises at least one suturing element that allows fixating the at least one outer lumen to the patient's body once it is cannulated.

8. The cannula of claim 1, wherein said at least one inner lumen or said at least one outer lumen further comprises one or more calibration marks.

9. The cannula of claim 1, wherein said at least one flow router further comprises a first internal flow channel position connection area from the at least one outer lumen through the at least one outer lumen connector unit then at least one inner lumen connector unit to the medical device.

10. The cannula of claim 9, wherein said at least one flow router further comprises a second internal flow channel from the medical device through the at least one inner lumen connector unit to the at least one inner lumen.

11. The cannula of claim 9, wherein the flow is reversed such that said first internal flow channel provides a flow path from the medical device through the at least one inner lumen connector unit to the at least one outer lumen connector unit, then to the outer lumen.

12. The cannula of claim 9, wherein the flow is reversed such that said second internal flow channel provides a flow path from the at least one inner lumen through the at least one inner lumen connector unit to the medical device.

13. The cannula of claim 1, wherein said at least one outer lumen and said at least one outer lumen connector unit are formed as a single piece.

14. The cannula of claim 1, wherein said at least one inner lumen connector unit further comprises a vertical separating wall and chambers for creating a separate flow channel via one or more lumen opening to the at least one inner lumen and a separate outer flow channel to the at least one outer lumen through the at least one outer lumen connector unit.

15. A process for installing a single lumen cannula in a patient and transforming said single lumen cannula into a dual lumen cannula, in real time, in vivo, the process comprising:

inserting an outer lumen into a patient's vascular system through use of an introducer, and optionally a guidewire, drawn through the outer lumen up to its distal end;

withdrawing the introducer and guidewire causing a small vacuum to form in the outer lumen, which is back filled with blood;

connecting at least one single flow connector to said outer lumen for use of said outer lumen as the single lumen cannula, such that said outer lumen is in coupling contact with said at least one single flow connector, and after said outer lumen has been installed in the patient;

converting said single lumen cannula to said dual lumen cannula by priming a inner lumen through use of a priming cap connected to a priming system, whereupon following completion of the priming, the priming cap is removed;

removing said at least one single flow connector from said outer lumen;

inserting said inner lumen within said outer lumen until an inner lumen connector unit fastens to an outer lumen connector unit;

connecting at least one dual flow connector to a proximal end of said inner lumen until said inner lumen connector unit is in coupling contact with said at least one dual flow connector, and after said outer lumen has been installed in the patient.

16. The process of claim 15, wherein said outer lumen is sutured to a skin of the patient by stitching regular sutures through a butterfly.

17. The process of claim 15, further comprising connecting at least one flow router to said inner lumen connector unit.

18. The process of claim 17, wherein one or more medical devices are connected to said at least one flow router.

19. A process for converting the dual lumen cannula of claim 17 into the single lumen cannula in the patient, in real time, in vivo, the process comprising:

decoupling and removing said at least one dual flow connector and said inner lumen from a proximal end of said outer lumen; and connecting at least one single flow connector to said outer lumen for use of said outer lumen as the single lumen cannula, such that said outer lumen is in coupling contact with said at least one single flow connector.

20. The process of claim 19, wherein upon converting said dual lumen cannula into the single lumen cannula, a second single lumen cannula is installed in the patient.

* * * * *